US011896318B2

(12) United States Patent
Stanton et al.

(10) Patent No.: US 11,896,318 B2
(45) Date of Patent: Feb. 13, 2024

(54) METHODS AND SYSTEMS FOR CONTROLLING A SURGICAL ROBOT

(71) Applicant: Mobius Imaging, LLC, Shirley, MA (US)

(72) Inventors: Russell Stanton, Lunenberg, MA (US); Gordon Row, Groton, MA (US); Edward Daley, Maynard, MA (US)

(73) Assignee: Mobius Imaging, LLC, Shirley, MA (US)

( * ) Notice: Subject to any disclaimer, the term of this patent is extended or adjusted under 35 U.S.C. 154(b) by 764 days.

(21) Appl. No.: 17/048,736

(22) PCT Filed: Apr. 19, 2019

(86) PCT No.: PCT/US2019/028276
§ 371 (c)(1),
(2) Date: Oct. 19, 2020

(87) PCT Pub. No.: WO2019/204699
PCT Pub. Date: Oct. 24, 2019

(65) Prior Publication Data
US 2021/0236207 A1      Aug. 5, 2021

Related U.S. Application Data

(60) Provisional application No. 62/659,981, filed on Apr. 19, 2018.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/74* (2016.02); *A61B 90/39* (2016.02);
(Continued)

(58) Field of Classification Search
CPC ......... A61B 34/20; A61B 34/10; A61B 34/74; A61B 90/39; A61B 2034/107; A61B 2034/2055; B25J 5/00
See application file for complete search history.

(56) References Cited

U.S. PATENT DOCUMENTS 8,118,488 B2    2/2012  Gregerson
9,283,048 B2    3/2016  Kostrzewski et al.
(Continued)

FOREIGN PATENT DOCUMENTS

WO    2018053282 A1    3/2018
WO    2018222470 A1    12/2018

OTHER PUBLICATIONS

International Search Report for Application No. PCT/US2019/028276 dated Aug. 19, 2019, 3 pages.
U.S. Appl. No. 16/389,606, filed Apr. 19, 2019.

*Primary Examiner* — Kyle O Logan
(74) *Attorney, Agent, or Firm* — Howard & Howard Attorneys PLLC

(57) ABSTRACT

Methods and systems for controlling a robotic arm include tracking a motion of a handheld device using a motion tracking system, and controlling a robotic arm to adjust at least one of a position and an orientation of an end effector of the robotic arm based on the tracked motion of the handheld device. Further embodiments include methods and systems for transferring a robotic arm from a mounting surface to a mobile cart that include tracking the location of the mobile cart relative to the robotic arm using a motion tracking system, and controlling the robotic arm to move the arm into a pose that facilitates transferring the robotic arm from the mounting surface to the mobile cart based on the tracked location of the mobile cart.

20 Claims, 15 Drawing Sheets

(51) Int. Cl.
*A61B 34/00* (2016.01)
*A61B 90/00* (2016.01)
*B25J 5/00* (2006.01)

(52) U.S. Cl.
CPC ........... *B25J 5/00* (2013.01); *A61B 2034/107* (2016.02); *A61B 2034/2055* (2016.02)

(56) References Cited

U.S. PATENT DOCUMENTS

| | | |
|---|---|---|
| 10,772,577 B2 | 9/2020 | Fortuna et al. |
| 2007/0071560 A1 | 3/2007 | Karonen |
| 2013/0158709 A1 | 6/2013 | Shi et al. |
| 2014/0003572 A1 | 1/2014 | Gregerson et al. |
| 2014/0139215 A1 | 5/2014 | Gregerson et al. |
| 2014/0265182 A1 | 9/2014 | Stanton et al. |
| 2014/0275953 A1 | 9/2014 | Gregerson et al. |
| 2017/0042625 A1* | 2/2017 | Sartor .................... B25J 9/1689 |
| 2018/0029221 A1 | 2/2018 | Tanaka et al. |
| 2018/0185113 A1* | 7/2018 | Gregerson ............. A61B 5/742 |
| 2018/0207794 A1* | 7/2018 | Sebring .................. B25J 5/007 |

* cited by examiner

METHODS AND SYSTEMS FOR CONTROLLING A SURGICAL ROBOT

RELATED APPLICATION

This application claims the benefit of priority to U.S. Provisional Application No. 62/659,981, filed Apr. 19, 2018, the entire contents of which are incorporated by reference herein.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained Using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include methods and systems for performing robot-assisted surgery.

Embodiments include a method for controlling a robotic arm that includes tracking a motion of a handheld device using a motion tracking system, and controlling a robotic arm to adjust at least one of a position and an orientation of an end effector of the robotic arm based on the tracked motion of the handheld device.

Further embodiments include a method for transferring a robotic arm from a mounting surface to which the robotic arm is attached during use to a mobile cart for storage and/or transport of the robotic arm, where the method includes tracking the location of the mobile cart relative to the robotic arm using a motion tracking system, and controlling the robotic arm to move the robotic arm into a pose that facilitates transferring the robotic arm from the mounting surface to the mobile cart based on the tracked location of the mobile cart.

Various embodiments include robotic systems including processors configured to perform operations of the embodiment methods disclosed herein. Various embodiments also include robotic systems including means for performing functions of the embodiment methods disclosed herein. Various embodiments also include non-transitory processor- and server-readable storage media having stored thereon processor-executable instructions configured to cause a processor to perform operations of the embodiment methods disclosed herein.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
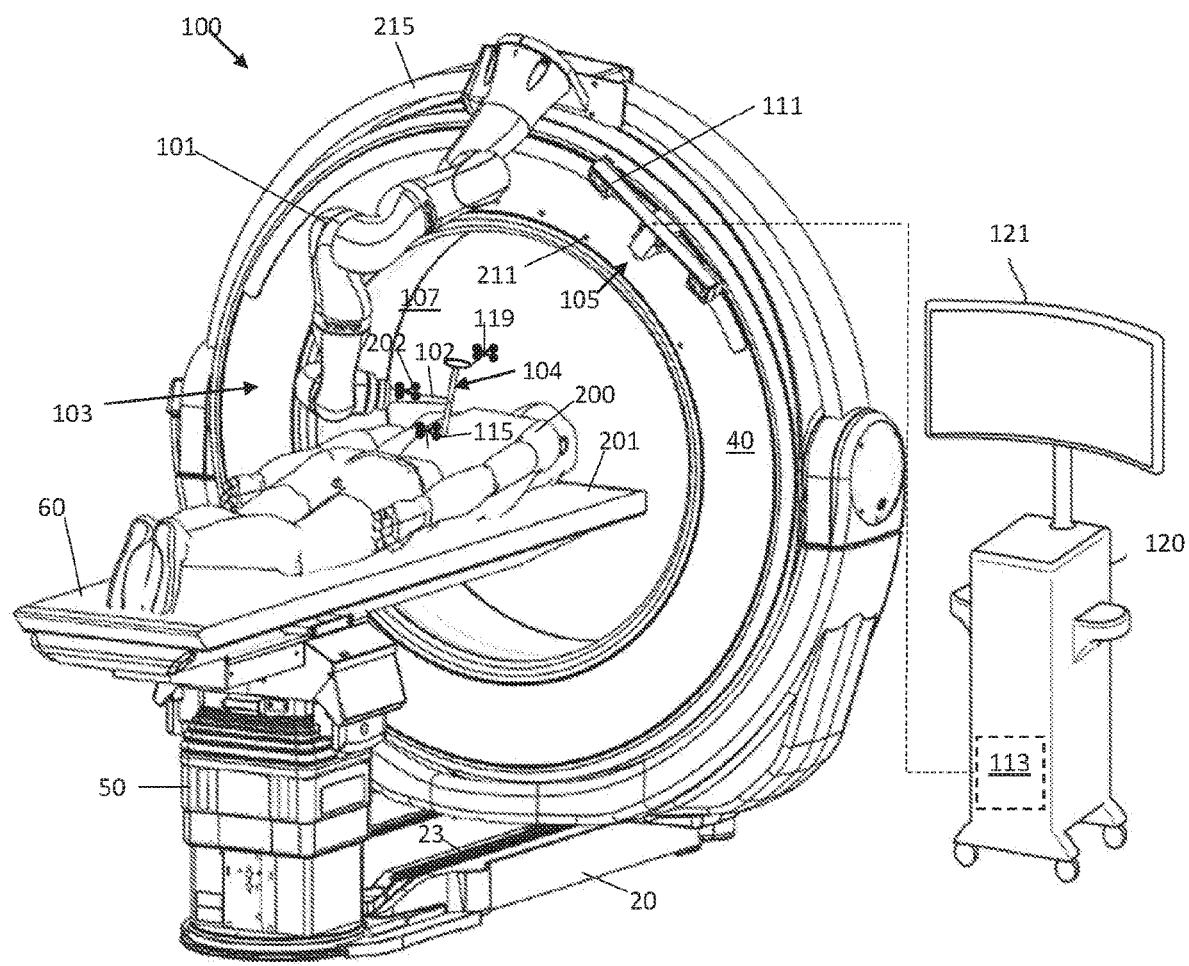
FIG. 1 is a perspective view of a system for performing robotically-assisted image-guided surgery according to an embodiment.

FIG. 1 illustrates a system 100 for performing robotically-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi-joint arm that includes a plurality of linkages connected by joints having actuator(s) and optional encoder(s) to enable the linkages to rotate, bend and/or translate relative to one another in response to control signals from a robot control system. The robotic arm 101 may be fixed to a support structure at one end and may have an end effector 102 at the other end of the robotic arm 101.

The imaging device 103 may be used to obtain diagnostic images of a patient 200, which may be a human or animal patient. In embodiments, the imaging device 103 may be an x-ray computed tomography (CT) imaging device. The patient 200 may be positioned within a central bore 107 of the imaging device 103 and an x-ray source and detector may be rotated around the bore 107 to obtain x-ray image data (e.g., raw x-ray projection data) of the patient 200. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure) or intra-operatively (i.e., during a surgical procedure) by positioning the patient 200 within the bore 107 of the imaging device 103. In the system 100 of FIG. 1, this may be accomplished by moving the imaging device 103 over the patient 200 to perform a scan while the patient 200 may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182, U.S. Patent Application Publication No. 2014/0275953 and U.S. Patent Application Publication No. 2017/0071560, the entire contents of all of which are incorporated herein by reference. In the embodiment shown in FIG. 1, the patient support 60 (e.g., surgical table) upon which the patient 200 may be located is secured to the imaging device 103, such as via a column 50 which is mounted to a base 20 of the imaging device 103. A portion of the imaging device 103 (e g an O-shaped imaging gantry 40) which includes at least one imaging component may translate along the length of the base 20 on rails 23 to perform an imaging scan of the patient 200, and may translate away from the patient 200 to an out-of-the-way position for performing a surgical procedure on the patient 200.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-Arm® surgical imaging system form Medtronic, plc. The imaging device 103 may also be a C-arm x-ray fluoroscopy device. In other embodiments, the imaging device 103 may be a fixed-bore imaging device, and the patient 200 may be moved into the bore of the device, either on a surgical support 60 as shown in FIG. 1, or on a separate patient table that is configured to slide in and out of the bore. Further, although the imaging device 103 shown in FIG. 1 is located close to the patient 200 within the surgical theater, the imaging device 103 may be located remote from the surgical theater, such as in another room or building (e.g., in a hospital radiology department).

The motion tracking system 105 shown in FIG. 1 includes a plurality of marker devices 119, 202, 115 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers, A 3D model of the space may be constructed in software based on the signals detected by the sensing device.

The motion tracking system 105 in the embodiment of FIG. 1 includes a plurality of marker devices 119, 202 and 115 and a stereoscopic optical sensor device 111 that includes two or more cameras (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and 115 and received by the cameras. The marker devices 119, 202, 115 may each include three or more (e.g., four) reflecting spheres, which the motion tracking system 105 may use to construct a coordinate system for each of the marker devices 119, 202 and 115. A computer 113 may be coupled to the sensor device 111 and may determine the transformations between each of the marker devices 119, 202, 115 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, a reference marker device 115 (e.g., reference arc) may be rigidly attached to a landmark in the anatomical region of interest (e.g., clamped or otherwise attached to a bony portion of the patient's anatomy) to enable the anatomical region of interest to be continually tracked by motion tracking system 105. Additional marker devices 119 may be attached to surgical tools 104 to enable the tools 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria innovation Inc. of Milwaukee, Wisconsin. Other tracking technologies, such as computer vision systems and/or magnetic-based tracking systems, may also be utilized.

The system 100 may also include a display device 121 as schematically illustrated in FIG. 1. The display device 121 may display image data of the patient's anatomy obtained by the imaging device 103. The display device 121 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 121, and may be shown overlaying the image data. In the embodiment of FIG. 1, the display 121 is located on a mobile cart 120. A computer 113 for controlling the operation of the display 121 may also be housed within the cart 120. In embodiments, the computer 113 may be coupled to the optical sensor device 111 and may also perform all or a portion of the processing (e.g., tracking calculations) for the motion tracking system 105. Alternatively, one or more separate computers may perform the motion tracking processing, and may send tracking data to computer 113 on the cart 120 via a wired or wireless communication link. The one or more separate computers for the motion tracking system 105 may be located on the imaging system 103, for example.

Figure 2:
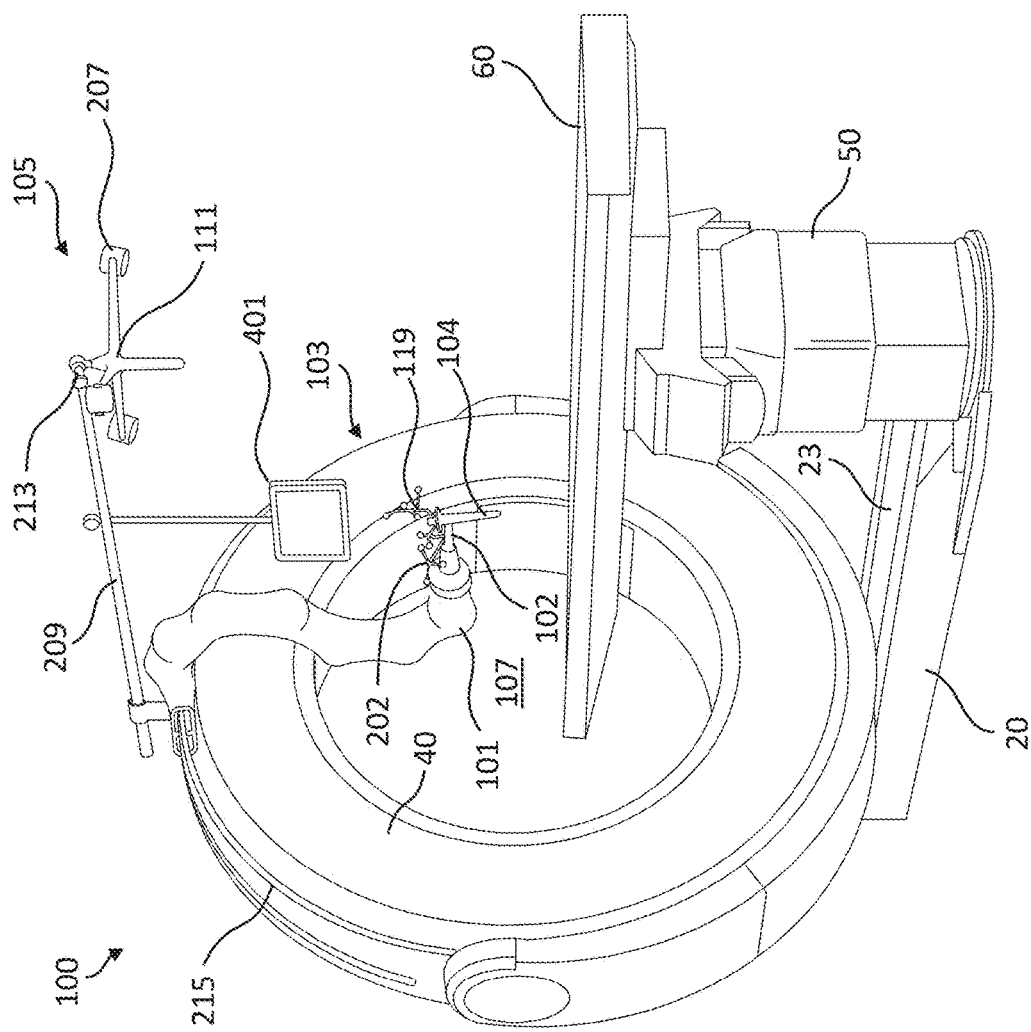
FIG. 2 shows an alternative embodiment of a system for performing robotically-assisted image-guided surgery having an optical sensing device for a motion tracking system on an arm extending from a gantry of an imaging system.

FIG. 2 illustrates an alternative embodiment in which the optical sensor device 111 includes a plurality of cameras 207 mounted to an arm 209 extending above the patient 200 surgical area. The arm 209 may be mounted to or above the imaging device 103. The arm 209 may also enable the sensor device 111 to pivot with respect to the arm 209 and/or the imaging device 103 (e.g., via one or more ball joints 213). The arm 209 may enable a user to adjust the position of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure. The positioning of the optical sensor device 111 on an arm 209 may also enable the cameras 207 to more easily view and track markers 211 (see FIG. 1) that may be located on the imaging device 103, such as on the outer surface of the gantry 40, which may be used during automatic registration of patient images, as described further below.

FIG. 2 also illustrates a display device that may comprise a handheld display device 401. As used herein, "handheld computing device" and "handheld display device" are used interchangeably to refer to any one or all of tablet computers, smartphones, pendant controllers, cellular telephones, personal digital assistants (FDA's), netbooks, e-readers, laptop computers, palm-top computers, wearable computers, and similar portable electronic devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands.

One or more handheld display devices 401 may be mounted to an arm 209 extending above the patient surgical area, as shown in FIG. 2. The arm 209 may also support the optical sensing device 111 for the motion tracking system 105, as described above. The one or more display devices 401 may be suspended from the arm 209, and the position of a display device 401 may be adjustable along the length of the arm 209. The display device 401 may be located within a sterile case or holder, such as described in U.S. patent application Ser. No. 15/701,063, filed on Sep. 11, 2017, which is incorporated by reference herein. In other embodiments, a handheld display device 401 may be mounted to the patient support 60 or column 50 or to any portion of the imaging system 103, or to any of the wall, ceiling or floor in the operating room, or to a separate cart. One or more handheld display devices 401 may be used in addition to or as an alternative to a conventional display device, such as a cart-mounted monitor display device 121 as shown in FIG. 1.

As shown in FIGS. 1 and 2, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. In further embodiments, the robotic arm 101 and/or the optical sensing device 111 (nay be mounted to a separate mobile shuttle, as described in U.S. patent application Ser. No. 15/706,210, filed on Sep. 15, 2017, which is incorporated by reference herein. Although a single robotic arm 101 is shown in FIGS. 1 and 2, it will be understood that two or more robotic arms 101 may be utilized.

Figure 3:
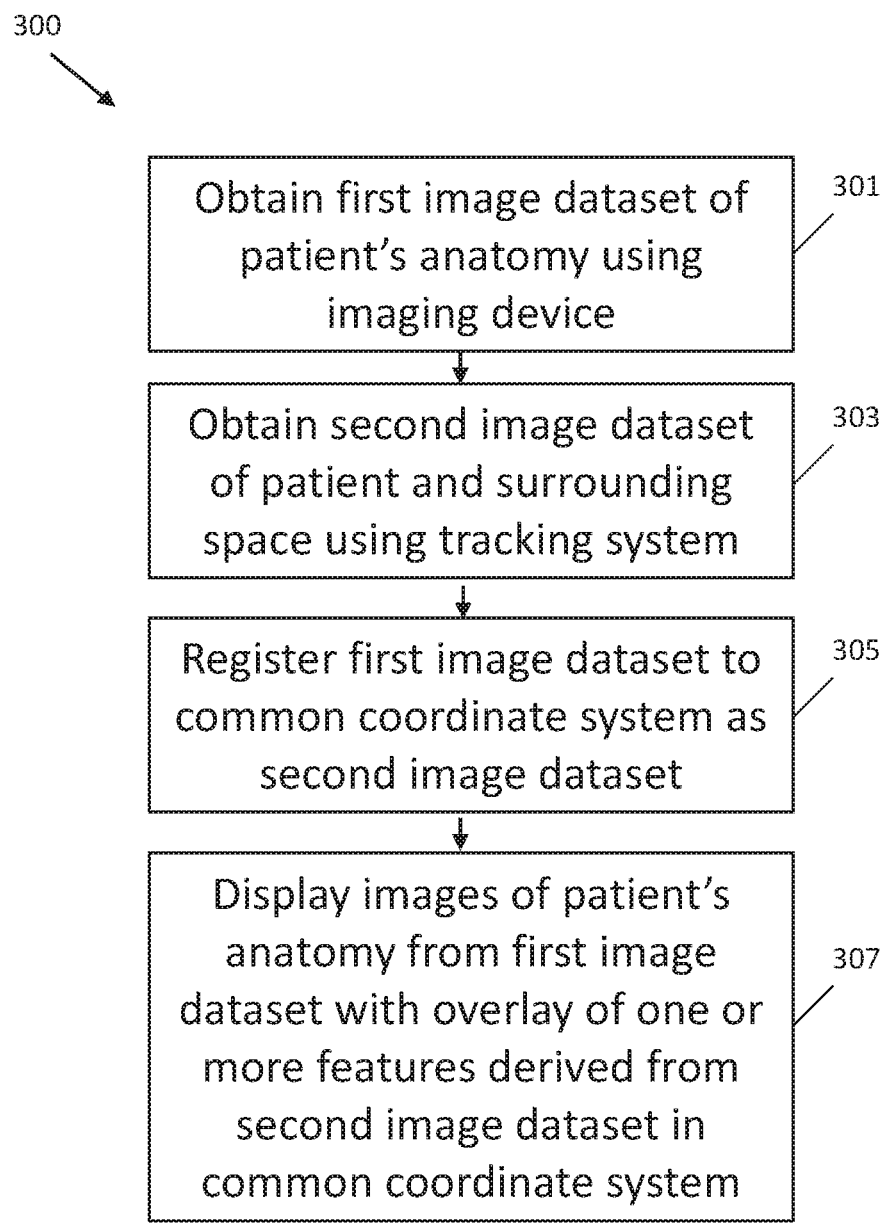
FIG. 3 is a process flow diagram illustrating a method for performing registration of patient image data for image-guided surgery.

FIG. 3 is a process flow diagram that illustrates a method 300 of registering patient images. Computer-assisted surgery techniques generally utilize a process of correlating a dataset representing a portion of the patient's anatomy that is to be operated on with the position of the patient at the time of the surgical intervention. The position of the patient may be determined based on a second image dataset which may include real-time camera image(s) from a motion tracking system 105 as described above. The correlation between these datasets may be accomplished computationally using software, and may be referred to as "patient registration." The registration method 300 of FIG. 3 may be implemented using one or more computing devices, such as computer 113 shown in FIG. 1.

In block 301 of method 300, a first image dataset of the patient's anatomy may be obtained using an imaging device, such as the imaging device 103 shown in FIGS. 1 and 2. The first image dataset may be a three-dimensional dataset (e.g., a 3D CT tomographic reconstruction, a 3D Mill dataset, etc.) representing at least a portion of the patient's anatomy, including the internal anatomy and/or structure(s) that are to be operated on (i.e., a surgically-relevant portion of the patient's anatomy). The first image dataset may be stored electronically in a memory. The first image dataset may be in any suitable format, such as in a file format that conforms to the Digital Imaging and Communications in Medicine (DICOM) standard.

In block 303 of method 300, a second image dataset of the patient and the surrounding patient space may be obtained using a motion tracking system, such as the motion tracking system 105 shown in FIGS. 1 and 2. The second image dataset may indicate the current position and/or orientation of the patient. The second image dataset may include at least one image of a marker device that may be obtained using an optical sensing device 111 (e.g., cameras 207). The marker device (e.g., reference arc 115) detected by the optical sensing device 111 may be in a known fixed relationship with the surgically-relevant portion of the patient's anatomy. The motion tracking system 105 may determine the transformation between the marker device 115 and the optical sensing device 111 (e.g., using well-known triangulation techniques), and may thereby determine the transformation between the sensing device 111 (e.g., camera 207 position) and the surgically-relevant portion of the patient's anatomy. The motion tracking system 105 may similarly determine transformations between each of the other marker devices (e.g., marker devices 119 and 202 in FIG. 1) and the optical sensing device 111. Each of the markers 115, 119 and 202 being tracked may then be placed within a common coordinate system. In embodiments, the common coordinate system may have an origin or zero point that may be considered to be fixed relative to the surgically-relevant portion of the patient's anatomy, and may also be referred to the patient coordinate system.

In block 305 of method 300, the first image dataset may be registered to the common coordinate system as the second image dataset (e.g., the patient coordinate system). This may include performing a rigid transformation to map each pixel or voxel of the first image dataset into corresponding 3D coordinates (i.e., x, y, z coordinates) of the common coordinate system. A number of techniques may be utilized for registering multiple image datasets. In one non-limiting example of a registration process for x-ray CT imaging data, a pre-scan calibration process may be used to precisely calculate (e.g., within 1 mm and/or 1°) the transformation between the isocenter of the x-ray gantry 40 and the optical sensing device 111. A set of markers 211 (e.g., 3 or more, such as 4-6 markers) may be provided on the surface of the gantry 40, as shown in FIG. 1. The markers 211 may be within the field of view of the optical sensing device 111 to enable the gantry 40 position to be tracked by the motion tracking system 105. A calibration phantom (not shown for clarity) having a marker device (e.g., similar to marker device 115 in FIG. 1) fixed thereto may be placed on the patient support 60 such that the marker device is also within the field of view of the optical sensing device 111. The motion tracking system 105 may determine the transformation between the gantry 40 coordinate system defined by the markers 211 and the optical sensing device 111 coordinate system as well as the transformation between the phantom coordinate system defined by the marker device on the phantom and the optical sensing device 111 coordinate system. These transformations may be used to determine the gantry-to-phantom transformation. The phantom may then be scanned using the imaging device 103. A set of elements (e.g., x-ray visible beads) that may be easily identified from the imaging data may be located in the phantom, where the geometry of these elements within the phantom coordinate system may be previously-known. An algorithm may be used to analyze the x-ray image data to identify the x-ray visible elements with respect to the center point of the image data, which corresponds to the isocenter of the gantry 40. Thus, the x-ray visible elements may be located in a coordinate system having an origin at the isocenter of the x-ray gantry 40, and the transformations between the isocenter and the phantom and the isocenter and the markers 211 on the gantry 40 may be calculated.

During a subsequent scan of the patient 200, the position and orientation of the patient 200 with respect to the isocenter of the imaging device 103 may be determined (i.e., by tracking the positions of the markers 211 on the gantry 40, which are known with respect to the isocenter, and the patient reference arc 115, which is known with respect to the surgically-relevant portion of the patient anatomy). This may enable the image data obtained during the scan to be registered into the patient coordinate system.

In an alternative embodiment, the position of the optical sensing device 111 may be known relative to the imaging system 103 with sufficient accuracy such that the image dataset of the patient's anatomy obtained using the imaging system 103 may be registered in the common coordinate system of the patient without the motion tracking system 105 needing to track the position or orientation of the imaging system 103. In embodiments, separate markers 211 on the gantry 40 of the imaging system 103 as shown in FIG. 2 may not be required or used. In some embodiments, the position of the optical sensing device 111 (e.g., the position of each of the cameras 207 as shown in FIGS. 1 and 2) may be known relative to the isocenter of the gantry of the imaging system 103, such as via a calibration process that may be performed at the factory or during installation or pre-calibration of the system. The gantry 40 and/or the optical sensing device 111 may include keying features (e.g., high-precision bolt patterns) where the optical sensing device 111 attaches to the gantry 40 to ensure that the position of the sensing device 111 on the gantry 40 remains accurately fixed. In embodiments where the camera(s) 207 may be movable relative to the gantry 40, high-precision encoders may precisely record and correct for any changes in camera position/orientation relative to the isocenter of the gantry 40. During imaging scans, the optical sensing device 111 may track the position and orientation of the patient 200 with respect to the camera position, which is in a known, fixed geometric relationship with the isocenter of the imaging device 103. The image data obtained during a scan may thus be registered into the common coordinate system of the patient without needing to first perform a calibration scan on a phantom, as described above.

In block 307 of method 300, images of the patient's anatomy from the first image dataset may be displayed with an overlay of one or more features derived from the second image dataset in the common coordinate system. The images may be displayed on a suitable display device, such as display 121 shown in FIG. 1. The images of the patient's anatomy may include 2D slices of a three-dimensional image dataset (e.g., a tomographic reconstruction) and/or a 3D volume rendering of all or a portion of the image dataset. In embodiments, images obtained using multiple imaging devices or imaging modalities may be fused and displayed in a common coordinate system. For example, the first image dataset of the patient's internal anatomy may be an x-ray CT scan. Another image dataset of the patient's internal anatomy, such as an MRI scan, may be combined with the x-ray CT data and displayed on the display 121. The MRI scan data may be registered into the common coordinate system using a similar registration process as described above. Alternately or in addition, an algorithm for snatching landmarks or fiducials identifiable from both image datasets may be used to merge the datasets for display.

The one or more features derived from the second image dataset that may be displayed overlaying the images of the patient's anatomy may include graphical depictions of a tool 104, an end effector 102 or another object that is tracked by the motion tracking system 105. The graphical depiction may be based on a known geometry of the tool 104, end effector 102 or another object. The graphical depiction may be a rendering of the actual size and shape of the object or may be a depiction of select features of the object, such as a location of a tip end of the object and/or an orientation of the object. The graphical depiction may also indicate a trajectory defined by the object (e.g., a ray extending from a tip end of the object into the patient) and/or a target point within the patient's anatomy that may be defined based on the position and/or orientation of one or more objects being tracked. In various embodiments, the tool 104 may be a pointer. The tool 104 may also be a surgical instrument, such as a needle, a cannula, dilator, a tool for gripping or cutting, an electrode, an implant, a drill bit, a screw, a screw driver, a radiation source, a drug and an endoscope. In embodiments, the end effector 102 of the robotic arm 101 may include a hollow tube or cannula that may be configured to hold one or more tools, such as a surgical instrument, and may be used to guide an instrument as it is inserted into the patient's body. Alternately, the end effector 102 itself may be or may include an instrument that may be inserted into the patient's body.

The motion tracking system 105 may repeatedly acquire new images from the optical sensing device 111, and the relative positions and/or orientations of objects within the field of view of the optical sensing device 111 may be updated with each acquisition of new images from the optical sensing device 111. The display 121 may be updated to reflect any change(s) in the position and/or orientation of the objects within the common coordinate system (e.g., relative to the patient reference arc 115), which may include adding additional graphical elements to depict new objects that are moved within the field of view of the optical sensing device 111 and removing graphical depictions of objects when they are no longer within the field of view of the optical sensing device 111. In some embodiments, the optical sensing device 111 may include a motorized system to enable the position and/or orientation of the camera(s) 207 to move to maintain the surgical area within the center of the field of view of the camera(s) 207.

Figure 4:
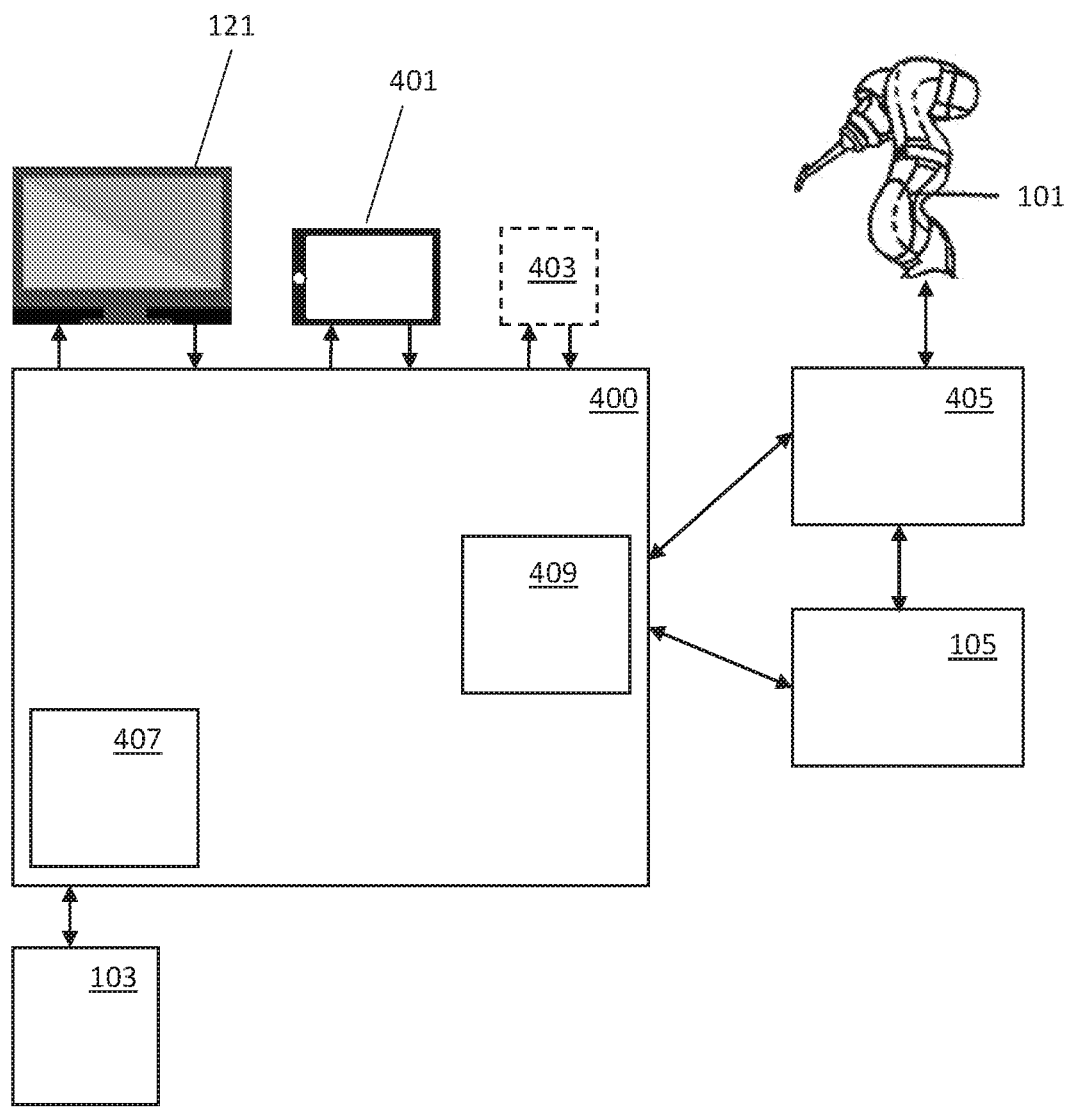
FIG. 4 is a block diagram schematically illustrating a system for robotically-assisted image-guided surgery according to an embodiment.

FIG. 4 is a component block diagram of an image-guided surgery system 400 according to an embodiment. The system 400 may be implemented using one or more computing devices, such as computer 113 shown in FIG. 1. The system 400 may be operatively coupled to a first display device 121, which may include a monitor that is fixed to a cart 120 or other structure (e.g., wall, ceiling, floor, imaging device, etc.) within the operating suite. The system 400 may also be operatively coupled to at least one additional display device 401, which may be a handheld computing device, as described above. The system 400 may also include an audio input/output component 403, which may include a speaker or other output component for outputting audible signals (e.g., audio instructions, alerts, etc.) and/or a microphone or other input component for receiving audio inputs (e.g., voice commands) that may be interpreted by the system 400. The system 400 may be implemented at least partially in software and may be based on one or more of the Image-Guided Surgery Toolkit (IGSTK), Visualization Toolkit (VTK) and Insight Segmentation and Registration Toolkit (ITK) development frameworks.

The system 400 may be configured to receive and store imaging data 407 (e.g., DICOM data) collected by an imaging device 103. The imaging data 407 may be received directly from the imaging device 103 or may be retrieved from another source, such as a remote server. The imaging data 407 may be imaging data that is obtained prior to a surgical procedure (e.g., pre-operative image data) and/or imaging data that is obtained during a surgical procedure (e.g., intra-operative image data). In embodiments, the system 400 may be configured to display the most-current image data 407 collected by the imaging device 103. The image data 407 may be registered to a common coordinate system as the tracking data 409 from the motion tracking system 105 in accordance with a registration method such as method 300 described above with reference to FIG. 3.

The system 400 may also receive tracking data 409 from a motion tracking system 105. The system 400 may be configured to repeatedly read the tracking data from the motion tracking system 105 indicating the current position/orientation of the patient and any other objects tracked by the motion tracking system 105. The system 400 may read the tracking data at a frequency (e.g., refresh rate) of greater than 100 Hz (e.g., 240 Hz). In embodiments, the tracking data from the motion tracking system 105 may include data to enable the system 400 to identify particular objects from within the tracking data. For example, each marker device (e.g., marker devices 115, 202 and 119 in FIG. 1) may include a unique characteristic (e.g., a unique geometric pattern of reflective markers, a unique flash pattern of active markers, etc.) to enable the marker device to be identified. These unique characteristics of the marker devices may be registered with particular objects or tools (e.g., associated with a particular object or tool in a database) by the system 400. The unique characteristics of the marker devices may be pre-registered in the system 400 and/or may be registered to particular objects or tools during the course of a surgical procedure. The system 400 may also include a library of graphical elements that may be associated with particular objects or tools (e.g., in a database). The system 400 may display graphical elements associated with the objects or tools being tracked by the motion tracking system 105 in the common coordinate system with the image data on the display(s) 119, 401.

The system 400 may include a user-interface component that may control the display of system information and/or graphical user interface elements on the display(s) 119 and 401. The system 400 may further process and implement user commands received from user interface devices. A user interface device, may include, for example, a touchscreen user interface which may be integrated with a display device 119, 401. In embodiments, a user interface device may alternately or additionally include one or more of a button, a keyboard, a joystick, a mouse, a touchpad, etc. which may be located on a display device 119, 401 and/or on a workstation (e.g., a workstation located on a cart 120). In embodiments, the user interface device(s) may also include a microphone (e.g., audio input/output component 403) that may receive voice commands that may be interpreted by the system (e.g., using voice recognition software). The user commands received via one or more user input devices may enable a user to control various functions of the system 400, such as changing what is shown on the display(s) 119, 401 (e.g., displaying different image datasets, displaying different slice(s) and/or different 3D rendering(s) within an image dataset, zooming in or out of an image, displaying different menu options, returning to a home screen, etc.). In embodiments, the user commands may enable a user to set one or more trajectories and/or target locations within the patient's anatomy. The system 400 may store the positions and/or orientations of user-defined trajectories or target locations within the common coordinate system, and may display graphical representations of such trajectories or target locations on the display(s) 119, 401.

The user commands received by the system 400 may also include commands for controlling the operation of other components, such as the imaging device 103, the motion tracking system 105 and/or a robotic arm 101. For example, for a robotically-assisted surgical procedure, the user command may include an instruction to move a robotic arm 101 to a particular position and/or orientation. The instruction to move the robotic arm 101 may be based on a user interaction with image data of the patient's anatomy that is displayed on a display device 119, 401. For example, the user may use the display device 119, 401 to define a particular trajectory with respect to the patient's anatomy and may send an instruction for the robotic arm 101 to move such that that the end effector 102 of the robotic arm 101 is positioned along the defined trajectory.

A robotic control system 405 may control the movement of one or more robotic arms 101. The robotic control system 405 may receive sensor data indicating the current parameters of the robotic arm 101 (e.g., robot position, joint angles, measured axis forces, motor currents) and may send motor control signals to drive the movement of the arm 101. In embodiments, the motion tracking system 105 may track the position of the robotic arm 101 (e.g., via marker device 202 on end effector 102 as shown in FIG. 1) to determine the position of the end effector 102 within the common coordinate system of the patient. A control loop, which may be executed using the image-guided surgery system 400, the motion tracking system 105 and/or the robotic control system 405, may continuously read the tracking data and the robot parameter data and may send instructions to the robotic control system 405 to cause the robotic arm 101 to Move to a desired position and orientation.

In various embodiments, display device 119 may be a primary display device (e.g., a monitor) that may be connected to the image-guided surgery system 400 by a wired or wireless link. In one embodiment, the system 400 may stream video data to the display device 119 over a suitable video data interface (e.g., an HDMI interface) and may also exchange other signals with the display device over a separate data connection (e.g., a USB connection).

In various embodiments, display device 401 may be a handheld computing device. A handheld display device 401 may generally be smaller and lighter than the primary display device 119 (e.g., monitor), and may in certain embodiments be referred to as a secondary display device. In some embodiments, display device 401 may be a mirror of display device 119 and may display all or a portion of the same information as is shown on display device 119. Alternately, display device 401 may display different information than is shown on display device 119. In some embodiments, display device 119 may be omitted, and handheld display device 401 may be the only display device operably connected to the image-guided surgery system 400. In such a case, display device 401 may be referred to as the primary display device. Further, although a single handheld display device 401 (i.e., a tablet computer) is shown in FIG. 4, it will be understood that multiple handheld display devices 401 may be simultaneously connected to and used with the system 400.

The handheld display device 401 may be coupled to the image-guided surgery system 400 by a wired or wireless communication link. In one embodiment, the handheld display device 401 may communicate with the system 400 over a wireless communication interface. The system 400 may stream digital video data (e.g., high-definition video) for display on the handheld display device 401, such as over a wireless local area network (WLAN) connection, including a IEEE 801.11 (e.g., WiFi) connection. The system 400 may also exchange other signals with the handheld display device 401 (e.g., control signals from the system 400 and/or user commands received at a user interface, such as a touchscreen, on the display device 401) over a wireless connection. The system 400 and the display device 401 may communicate over any suitable wireless protocol or standard, such as over a IEEE 802.15x (e.g., a BLUETOOTH®) connection.

An image-guided surgical system 400 according to various embodiments may provide a plurality of modes for displaying patient information. For example, a first display mode may include displaying a 3D image dataset (e.g., an x-ray CT, MRI, sonogram, PET or SPECT image dataset) in multiple two-dimensional slices corresponding to anatomic planes (e.g., axial, sagittal, coronal planes) transecting the patient. This is illustrated in the screenshot of a display device shown in FIG. 5. The display device may be a display device 119 (e.g., monitor) as shown in FIG. 1 or a handheld display device as shown in FIGS. 2 and 4. The display screen 500 in this example illustrates four different patient images in four quadrants of the display screen 500. Three of the quadrants (i.e., top left, top right and bottom left quadrants of display screen 500) depict different two-dimensional slices 501, 503, 505 of CT image data. A fourth quadrant (i.e., lower left quadrant of display screen 500) includes a 3D volume rendering 507 illustrating a "virtual" view of anatomic feature(s) (e.g., bony structures or other discrete internal anatomic features). The two-dimensional slices 501, 503, 505 correspond, respectively, to views taken along axial, sagittal and coronal planes through the patient 200.

Figure 5:
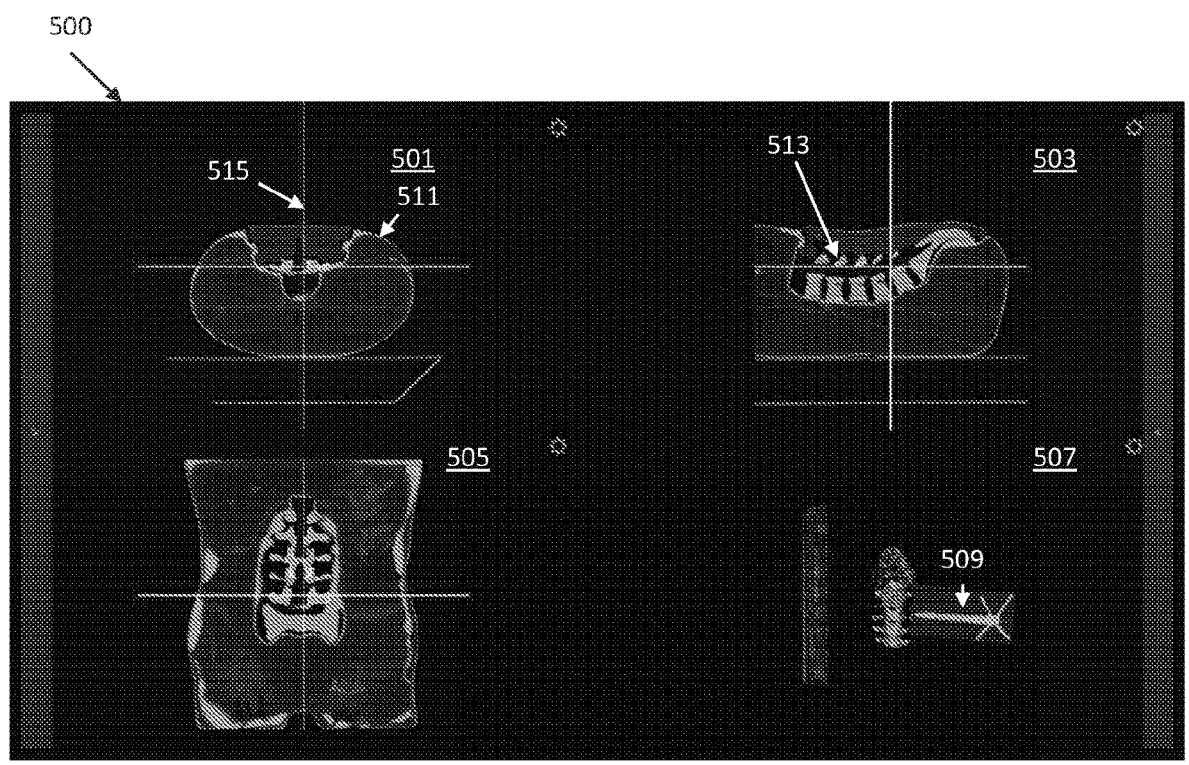
FIG. 5 illustrates a display screen of a display device in an image-guided surgery system according to an embodiment.

The display screen 500 may also display graphical elements illustrating the relationship of each slice 501, 503, 505 relative to the other slices shown on the display screen 500. For example, as shown in FIG. 5, the axial slice 501 image data may include an overlay of a cross pattern 515 showing the intersection of the axial slice 501 with the planes corresponding to the sagittal and coronal slices 503 and 505 shown on the display screen 500. Similar cross patterns 515 may be displayed overlaying the display of image data in the sagittal and coronal slices 503 and 505. The display screen 500 may also include graphical representations or renderings of other objects or tools tracked by the motion tracking system 105. In the example of FIG. 5, a graphical representation of a tool 509 is shown in the lower right quadrant of the display screen 500. The graphical representation of the tool 509 may illustrate the position and orientation of the tool relative to the anatomic features depicted in the 3D volume rendering 507. Similar graphical elements may be displayed in the 2D slice images 501, 503 and 505 to illustrate the position and/or orientation of one or more objects with respect to the patient.

It will be understood that the four-quadrant view shown in FIG. 5 is one possible implementation of a display of patient information on a display device 119, 401. Other possible display modes are possible. For example, rather than illustrating multiple different images (e.g., slices) from a patient image dataset (e.g., reconstructed volume), the display screen 500 may show only a single image (e.g., a single axial, sagittal or coronal slice 501, 503, 505 or a single 3D volume rendering 507). The display screen 500 may illustrate only two slices corresponding to different anatomic planes (e.g., axial and sagittal, axial and coronal, or sagittal and coronal slices), or may illustrate a single slice along with a 3D volume rendering. In some embodiments, the display screen 500 may illustrate multiple two-dimensional slices corresponding to the same anatomic planes (e.g., multiple axial, sagittal and/or coronal slices taken through different sections of the reconstructed volume) and/or multiple 3D volume renderings viewed from different angles. The different images and display modes of the display screen 500 may be customizable based on user selections, which may be made via a user input device and/or user voice commands. In embodiments, the user may be able to select (e.g., scroll through) different patient images, such as sequentially illustrating multiple axial, sagittal and/or coronal slices taken through different sections of the reconstructed volume, or sequentially illustrating multiple 3D volume renderings viewed from different angles. The display screen 500 may also display slices along oblique planes taken through the reconstructed volume. The user may also have the capability to control the magnification of images, such as by zooming into or out from a particular portion of an image shown in the display screen 500. The user may control the selection of patient images for display using a user input device, voice commands and/or via a separate tool, such as a pointer device. In some embodiments, the intersection of the three image planes (i.e., axial, sagittal and coronal) shown on the display panel 500 may coincide with a target position within the patient's body. The surgeon may use the display panel 500 as a "virtual cutting tool" to move through the various slices/views of the patient image volume and to identify and select a target region for a surgical intervention.

The user (e.g., a surgeon) may be able to set one or more target positions and/or trajectories within the patient 200. There may be a variety of ways to set a trajectory or target location. For example, the surgeon may move through different views of the patient image data by manipulating a tool (e.g., a pointer/stylus device and/or an end effector of a robotic arm) over the patient 200, where the tool may define a unique trajectory into the patient. The tool may be tracked within the patient coordinate system using the motion tracking system 105. In some embodiments, an imaginary ray projected forward from the tip end of the tool may define the unique trajectory into the patient, which may be graphically depicted on the display screen 500. A target location along the unique trajectory may be defined based on a pre-determined offset distance from the tip end of the tool. Alternately, the surgeon may directly manipulate and interact with the displayed image data to identify a particular target or trajectory, such as using a workstation computer. A particular target point or trajectory may be set by the system 400 in response to an input event, which may include, for example, a voice command, a touch event on a touchscreen interface, and/or an input on a user interface device (e.g., a keyboard entry, a mouse click, a button push, etc.). In embodiments, the surgeon may set a target position and/or trajectory by interacting with image data displayed on a display device, such as display devices 119 and/or 401. For example, the surgeon may define a target point and/or trajectory in the patient 200 by selecting one or more points on a display screen 500 of a display device 119, 401 (e.g., marking the points using a stylus, a cursor or mouse pointer, or a touch on a touchscreen user interface). To define a trajectory, for instance, the user may select two or more points in the image data (e.g., a target point and an entrance point on the skin of the patient). In embodiments, the user may be able to make fine adjustments to a selected target point and/or trajectory using any suitable user interface device. Multiple target points and/or trajectories may be set and saved in a memory (e.g., in an image-guided surgery system 400 as illustrated in FIG. 4), where each target point and/or trajectory may be saved in association with a unique identifier (e.g., file name).

In embodiments, the display screen 500 may display graphical element(s) overlaying the image data corresponding to one or more target locations and/or trajectories that are set by the user. For example, defined target locations may be illustrated as identifiable dots or points in the image data, which may be color coded and/or labeled on the display screen 500 to enable easy visualization. Alternately or in addition, defined trajectories may be depicted as identifiable lines or line segments in the image data, which may be similarly color coded and/or labeled. As discussed above, the display screen 500 may also display graphical elements associated with particular tools or objects, including invasive surgical tools or instruments, that are tracked by the motion tracking system 105. In embodiments, the display screen 500 may depict at least a portion (e.g., a tip end) of a surgical instrument as it is inserted into the patient 200, which may enable the surgeon to track the progress of the instrument as it progresses along a defined trajectory and/or towards a defined target location in the patient 200. In some embodiments, the patient images on the display screen 500 may be augmented by graphical illustrations of pre-calibrated tools or implants (e.g., screws) that are located within the patient 200.

The at least one robotic arm 101 may aid in the performance of a surgical procedure, such as a minimally-invasive spinal surgical procedure or various other types of orthopedic, neurological, cardiothoracic and general surgical procedures. In some embodiments, when the robotic arm 101 is pointed along a set trajectory to a target position, the robotic arm 101 may maintain a rigid or fixed pose to enable the surgeon to insert an instrument or tool through a cannula or similar guide arranged along a vector that coincides with the predefined trajectory into the body of the patient 200. The cannula may be a portion of the end effector 102 of the robotic arm 101 or it may be separate component that is held by the end effector 102. The cannula/guide may be positioned by the robotic arm 101 such that the central axis of the cannula is collinear with the pre-defined trajectory into the patient 200. The surgeon may insert one or more invasive surgical instrument through the cannula/guide along the trajectory and into the body of the patient to perform a surgical intervention. Alternately, the end effector 102 itself may comprise a surgical instrument that may be moved into the body of the patient, such as, without limitation, a needle, a dilator, a tool for gripping, cutting or ablating tissue, an implant, a drill bit, a screw, a screw driver, a radiation source, a drug and/or an endoscope.

Various embodiments include methods and systems for controlling a robotic arm 101 to adjust a position and/or orientation of the end effector 102 of the robotic arm 101. A robotic arm 101 such as shown in FIGS. 1 and 2 may be moved autonomously to a particular pose by the robotic control system 405 (e.g., in accordance with a robotic motion planning algorithm). For example, in response to a user command for the robotic arm 101 to go to a pre-set target position or trajectory, the robotic control system 405 may control the robotic arm 101 to autonomously move the arm 101 to a pose with the tip end of the end effector 102 pointing along the pre-set trajectory to the target position. Optionally, the robotic arm 101 may also operate in a hand guiding mode in which the movement of the robotic arm 101 may be controlled based on a force applied by a user to the arm (e.g., using torque and/or force sensing feedback to the robotic control system 405).

In various embodiments, the robotic arm 101 may also operate in a mode in which the robotic arm 101 is controlled to adjust a position and/or orientation of an end effector 102 of the robotic arm 101 based on a tracked motion of a handheld device. A motion tracking system 105 such as described above may track the motion of a handheld device (e.g., an instrument 104 having a marker device 119 attached thereto). The tracked motion of the handheld device may be provided to the robotic control system 405 so that the robotic control system 405 may control the robotic arm 101 to adjust the position and/or orientation of the end effector 102 based on the tracked motion. As used herein, this mode of controlling the motion of the robotic arm 101 may be referred to as "follow" mode.

Figure 6:
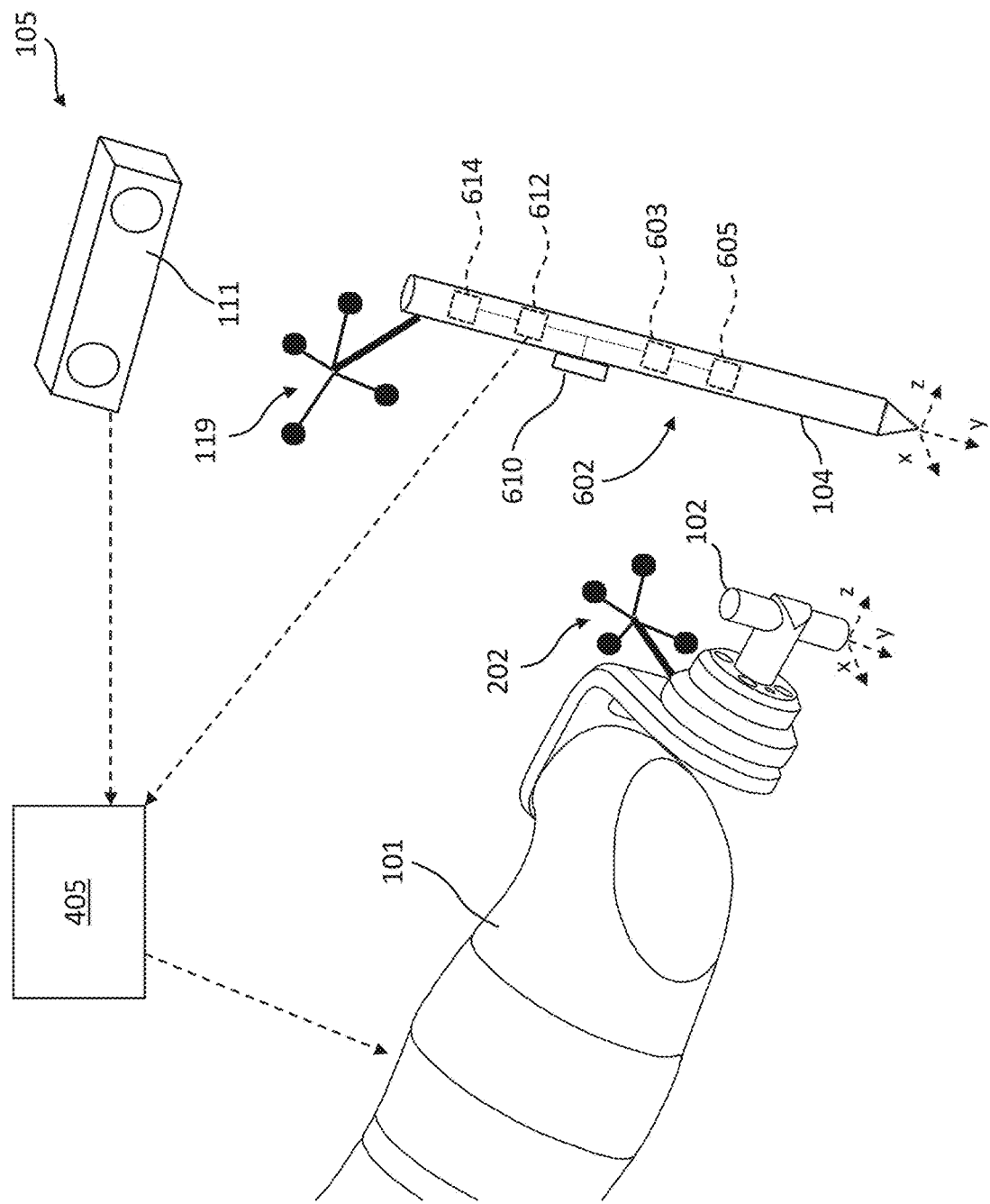
FIG. 6 illustrates a portion of a robotic arm having an end effector and a handheld device having a marker device that enables the handheld device to be tracked using a motion tracking system.

FIG. 6 illustrates a portion of a robotic arm 101 including an end effector 102, and a handheld device 104 having a marker device 119 that enables the handheld device 104 to be tracked using a motion tracking system 105. The handheld device 104 may be any device that may be held and manipulated by a user. The handheld device 104 may be a stylus or pointer device or a surgical instrument (e.g., a needle, screw driver, scalpel, awl, etc.) having an attached marker device 119. Alternately, the handheld device 104 may be a dedicated device used only for robot motion control. In embodiments, the handheld device 104 may be a separate component that is not physically connected or coupled to the robotic arm 101.

The system may enter the "follow" mode for controlling the motion of the robotic arm 101 in response to an input event from the user. The input event may be, for example, a voice command, a touch event on a display screen, a button push, a mouse/keyboard click, depression of a foot pedal, etc. In some embodiments, the handheld device 104 may have a marker device 119 with a unique marker pattern such that the system may automatically enter the "follow" mode when the handheld device 104 is brought within the field-of-view of the optical sensor(s) 111 of the motion tracking system 105.

As described above, the motion tracking system 105 may track the motion of the handheld device 104 in three-dimensional space, including the translation of the handheld device 104 (i.e., x, y and z translation) as well as rotational movement of the handheld device 104 (i.e., yaw, pitch and roll rotation). Tracking data corresponding to the motion of the handheld device 104 may be provided to the robotic control system 405. The robotic control system 405 may perform motion planning based on the received tracking data and send control signals to the robotic arm 101 to cause the arm to perform a movement based on the tracked motion of the handheld device 104. In the embodiment of FIG. 6, for example, a translation of the handheld device 104 in one or more directions (i.e., ±x, y, and/or z directions) may result in a corresponding translation of the end effector 102 in the same direction(s). Similarly, a tracked rotational motion of the handheld device 104 (i.e., yaw, pitch and/or roll rotation) may result in a corresponding rotation of the end effector 102 in the same direction(s). In embodiments, the end effector 102 may "follow" the motion of the handheld device 104.

When operating in "follow" mode, the end effector 102 of the robotic arm 101 may perform a movement (i.e., translation and/or rotation) corresponding to a relative movement (translation and/or rotation) of the handheld device 104. The handheld device 104 may be located and moved in an area that is away from the surgical site, and may avoid obstacles and sterility concerns associated with the surgical site. The user may also freely choose the starting position of their hand when using the handheld device as a control mechanism or "air mouse" for guiding the movements of robotic arm 101.

Figure 7:
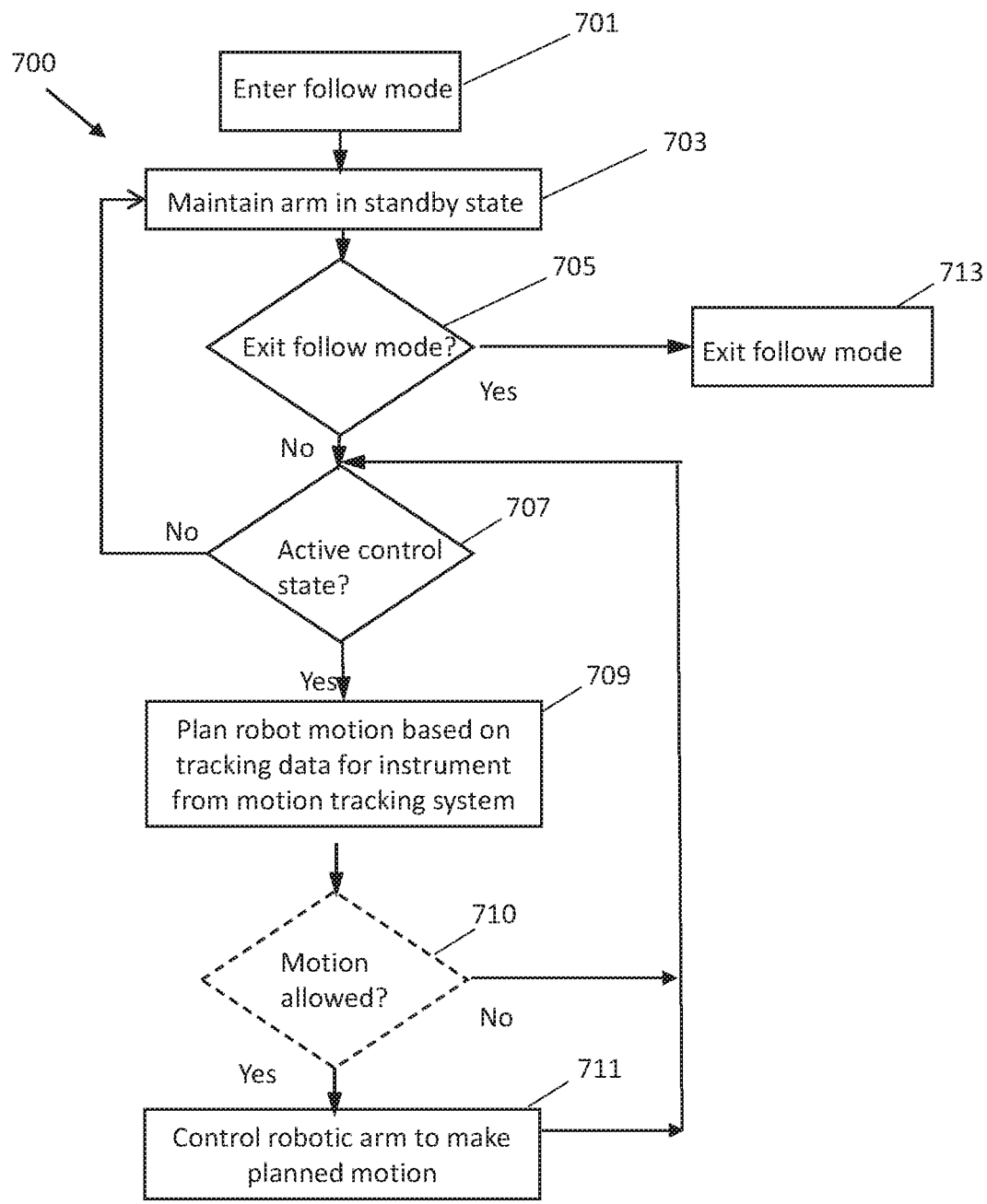
FIG. 7 is a process flow diagram illustrating an embodiment method for controlling a robotic arm based on the tracked motion of a handheld device.

FIG. 7 is a process flow diagram illustrating one embodiment of a method 700 for controlling a robotic arm based on the tracked motion of a handheld device. Method 700 may be implemented as a control loop on a processor of a robotic control system 405, such as described above with reference to FIGS. 4 and 6. In block 701 of method 700, the robotic control system 405 enters "follow" mode, which may be in response to a user input event, as described above. In block 703, the robotic control system 405 may proceed to a standby state in which the robotic arm is not moved.

In determination block 705, the robotic control system 405 may determine whether the system 405 is still operating in follow mode. In response to determining that the system 405 is still operating in follow mode (i.e., determination block 705="Yes"), the robotic control system 405 may determine whether the robotic arm 101 is in an active control state in determination block 407. The system 405 may remain in the standby state (i.e., block 703) in response to determining that the robotic arm 101 is not in an active control state (i.e., determination block 707="No").

As used herein, an active control state means that the robotic arm 101 is enabled to move in response to control signals received from the robotic control system 405. In some embodiments, the robotic control system 405 may determine whether the robotic arm is in an active control state in determination block 707 based on whether or not a user input component is actuated. For example, controlling the motion of the robotic arm may require some form of continuous activation by the user. This may help prevent unintentional movement of the robotic arm 101. The user input component that must be actuated to actively control the robotic arm 101 may be a button or similar apparatus (e.g., a foot pedal, pressure-sensitive pad, etc.) that must be pressed or held down to enable movement of the robotic arm 101.

In the embodiment of FIG. 6, the user input component may be a button. 610 on the handheld device 104. The handheld device 104 may include circuitry 612 configured to detect an input event (e.g., a button push) at the user-interface component and transmit a signal (e.g., a motion-enable signal) that may be received by the robotic control system 405. In some embodiments, the circuitry 612 may include wireless transceiver circuitry 614 configured to transmit signals wirelessly using a suitable wireless communication protocol or standard (e.g., an IEEE 802.15x (BLUETOOTH®) connection or IEEE 802.11 (WiFi) connection). The handheld device 104 may include a power supply 614 (e.g., battery source) to provide power to electronic components of the device 104. Alternately, the handheld device 104 may include a wired link for providing power and/or transmitting signals.

Alternately or in addition, the robotic control system 405 may determine whether the robotic arm is in an active control state in determination block 707 based on whether the robotic control system 405 is receiving tracking data from the motion tracking system 105 corresponding to the current position and/or orientation of the handheld device 104. In particular, the robotic arm 101 may only operate in an active control state while the robotic control system 405 is receiving up-to-date tracking data for the handheld device 104. The robotic arm 101 may operate in an active control state when, for example, the handheld device 104 is within the field-of-view of the optical sensor(s) 111 and the marker device 119 is not obstructed. In addition, operation in the active control state may optionally also require the user to actuate a user input component (i.e., continuous activation).

In response to determining that the robotic arm is in an active control state (i.e., determination block 705="Yes"), the robotic control system 405 may plan a movement of the robotic arm 101 based on the tracked movement of the handheld device 104 in block 709. In various embodiments, the robotic control system 405 may determine a change in position and/or orientation of the handheld device 104 between an initial position/orientation and a subsequent position and/or orientation. Based on the change in position and/or orientation of the handheld device 104, the robotic control system 405 may then determine a corresponding change in position and/or orientation of the end effector 102 of the robotic arm 101. In embodiments, the robotic control system 405 may utilize a motion planning algorithm (e.g., based on the inverse kinematics of the robotic arm) to plan the motion(s) of the robotic arm 101 to cause the change in the end effector 102 position and/or orientation.

In embodiments, the robotic control system 405 may determine whether a planned robot motion is allowed in optional determination block 710. For example, the robotic control system 405 may include a collision model with pre-defined "no go" space(s) in order to prevent the robotic arm 101 from colliding with the patient or other objects. A planned robot motion may not be allowed if it would result in the robotic arm 101 violating a "no go" space. In response to determining that the planned robot motion is not allowed (i.e., determination block 710="No"), the robotic control system 405 may return to determination block 705. Optionally, the robotic control system 405 may provide feedback to the user (e.g., audio, visual and/or haptic feedback) to indicate that the planned robot motion is not allowed. In response to determining that the planned robot motion is allowed (i.e., determination block 710="yes"), the robotic control system 405 may proceed to block 711.

In block 711, the robotic control system 405 may cause the robotic arm 101 to move (e.g., via sending control signals to the arm 101) in accordance with the movement planned in block 709. In particular, the robotic control system 405 may adjust the position and/or orientation of the end effector 102 of the robotic arm 101 based on the tracked motion of the handheld device 104. The display screen 500 of a display device 121, 401 may show a graphical depiction of the end effector 102 overlaying patient images as the robotic arm 101 is moved.

The method 700 may then return to determination block 705 to determine whether the robotic control system 405 remains in an active control state. If the robotic control system 405 determines that it is still in an active control state determination block 705="Yes"), then the robotic control system 405 may plan an additional movement of the robotic arm 101 based on the tracked movement of the handheld device 104 in block 709, determine whether the planned movement is allowed in optional determination block 710, and may control the robotic arm 101 to cause the robotic arm 101 to make the (allowed) planned movement in block 711. While the robotic arm remains in an active control state (i.e., determination block 705="Yes"), then the robotic control system 405 may repeatedly cycle through the operations of blocks 709 through 711 to control the robotic arm 101 to move the end effector 102 based on the detected movement (s) of the instrument 104 tracked by the motion tracking system 104.

In response to determining that the robotic arm is no longer in an active control state (i.e., determination block 707="No"), the robotic control system 405 may maintain the robotic arm 101 in a standby state in block 703. The robotic arm 101 may remain in a standby state until either the robotic control system 405 determines that the system 405 should exit the follow mode (i.e., determination block 705="Yes"), or the robotic arm 101 again enters an active control state (i.e., determination block 707="Yes"). The robotic control system 405 may determine that the system 405 should exit the follow mode (i.e., determination block 705="Yes") based on a user input event, and may exit the follow mode in block 413.

In embodiments, the handheld device 104 may be tracked using an inertial navigation method as an alternative or in addition to an optical-based tracking method. In the embodiment shown in FIG. 6, the handheld device 104 includes an inertial measurement unit 602 in addition to the marker device 119 for an optically-based motion tracking system 105, as described above. In embodiments, the inertial measurement unit 602 may enable redundant motion tracking of the handheld device 104. In particular, the position and/or orientation of the handheld device 104 may continue to be tracked when there is a loss of tracking by the optically-based motion tracking system 105, such as when the line of sight between marker device 119 and optical sensing device 111 is temporarily obscured. A similar inertial measurement unit 602 may also be located on the robotic arm 101, such as on or proximate to the end effector 102, to enable inertial motion tracking of the end effector 102.

The inertial measurement unit 602 may include a three-axis accelerometer 603 and a three-axis gyroscope 605. The accelerometer 603 and gyroscope 605 may be fabricated utilizing MEMS technology. The accelerometer 603 and gyroscope 605 may be separate components (e.g., chips) located in the handheld device 104 or may be integrated on a single device (e.g., integrated circuit). The handheld device 104 may also include circuitry 612 coupled to the accelerometer 603 and gyroscope 605 that may be configured to read output signals from these components 603, 605. The accelerometer 603 may output signals measuring the linear acceleration of the handheld device 104, preferably in three-dimensional space. The gyroscope 605 may output signals measuring the angular velocity of the handheld device 104, preferably also in three-dimensional space. The signals from the accelerometer 603 and gyroscope 605 may be processed using a suitable processor, such as a computer 113, to determine the position and orientation of the handheld device 104 with respect to an initial inertial reference frame via a dead reckoning technique. In particular, integrating the angular velocity measurements from the gyroscope 605 may enable the current orientation of the handheld device 104 to be determined with respect to a known starting orientation, Integrating the linear acceleration measurements from the accelerometer 603 may enable the current velocity of the handheld device 104 to be determined with respect to a known starting velocity. A further integration may enable the current position of the handheld device 104 to be determined with respect to a known starting position.

In embodiments, measurement data from the inertial measurement unit 602 may transmitted from the handheld device 104 to a separate computing device (e.g., computer 113) via a wired or wireless link. In embodiments, the data may be transmitted wirelessly using a suitable wireless communication protocol or standard (e.g., an IEEE 802.15x (BLUETOOTH®) or IEEE 802.11 (WiFi) connection), as described above. The computer 113 may perform the inertial navigation calculations to determine the position and orientation of the handheld device 104 in three-dimensional space, and preferably within the common, patient-centric coordinate system. The inertial navigation calculations may be initialized with a known initial position, orientation and/or velocity of the handheld device 104, which may be or may be derived from the most recent tracking data from the motion tracking system 105.

In some embodiments, the robotic control system 405 may control the robotic arm 101 to provide a pre-determined motion scaling between the movement of the handheld instrument 104 detected by the motion tracking system 105 and the corresponding movement of the robotic arm 101. As used herein, "motion scaling" refers to the conversion of the tracked movements of the handheld device 104 to the movement of a portion of the robotic arm 101 (e.g., the end effector 102). The motion scaling may be linear, and may be expressed as a ratio of device 104 movement to end effector 102 movement (i.e., X:Y, where X is the displacement and/or rotation of the handheld device 104 and Y is the corresponding displacement and/or rotation of the end effector 102). In some embodiments, the relationship between the handheld device 104 movement and the end effector 102 movement may be non-linear. For example, the ratio X:Y between handheld device 104 movement and end effector 102 movement may increase as a function of the proximity of the end effector 102 to the surgical site. In particular, as the end effector 102 is moved closer to the surgical site, the movements of the handheld device 104 may result in progressively smaller movements of the end effector 102.

The motion scaling between the instrument 104 and the end effector 102 may be a fixed parameter. Alternately, the motion scaling may be adjustable by the user. For example, a motion scaling factor applied by the robot control system 405 may be adjusted by the user via a user-input event, such as a voice command, a touch event on a display screen, a button push, a mouse/keyboard click, depression of a foot pedal, etc. In one non-limiting example, a first motion scaling factor may be utilized for gross movements of the robotic arm 101, and a second motion scaling factor may be utilized for fine movements of the robotic arm 101. The first motion scaling factor may be useful for moving the robotic arm 101 into and out of the surgical area, and the second motion scaling factor may be utilized for making precise adjustments to the position and/or orientation of the end effector 102 of the arm 101. In one example, the first motion scaling factor may provide an ~1:1 ratio of handheld device 104 movement to robot end effector 102 movement, and the second motion scaling factor may provide a larger ratio (e.g., a 2:1-10:1 ratio) of handheld device 104 movement to robot end effector 102 movement. It will be understood that the robotic control system 405 may apply more than two different motion scaling factors to control the movement of the robotic arm 101 based on the handheld device 104 with varying levels of granularity. Further, in some embodiments, the motion scaling factor may provide a ratio of handheld device 104 movement to end effector 102 movement that is less than 1:1, such that motions of the handheld device 104 are amplified in the corresponding motions of the robotic arm 101.

In some embodiments, while operating in the follow mode, the robotic control system 405 may control the movement of the robotic arm 101 in response to the detected movement of the handheld device 104 so as to limit the speed and/or torque of the robotic arm 101. The robotic control system 405 may be also programmed to apply restrictions on the distance and/or speed in which the robotic arm 101 may move in response to movements of the handheld device 104. This may provide an important safety function in the case of inadvertent movements of the handheld device 104 rapidly or over a long distance. In some embodiments, the robotic control system 405 may also control the movement of the robotic arm 101 to smooth out the movements of the handheld device 104 and/or to ignore minor tremors or vibrations of the handheld device 104 by implementing tremor filtering.

Figure 8:
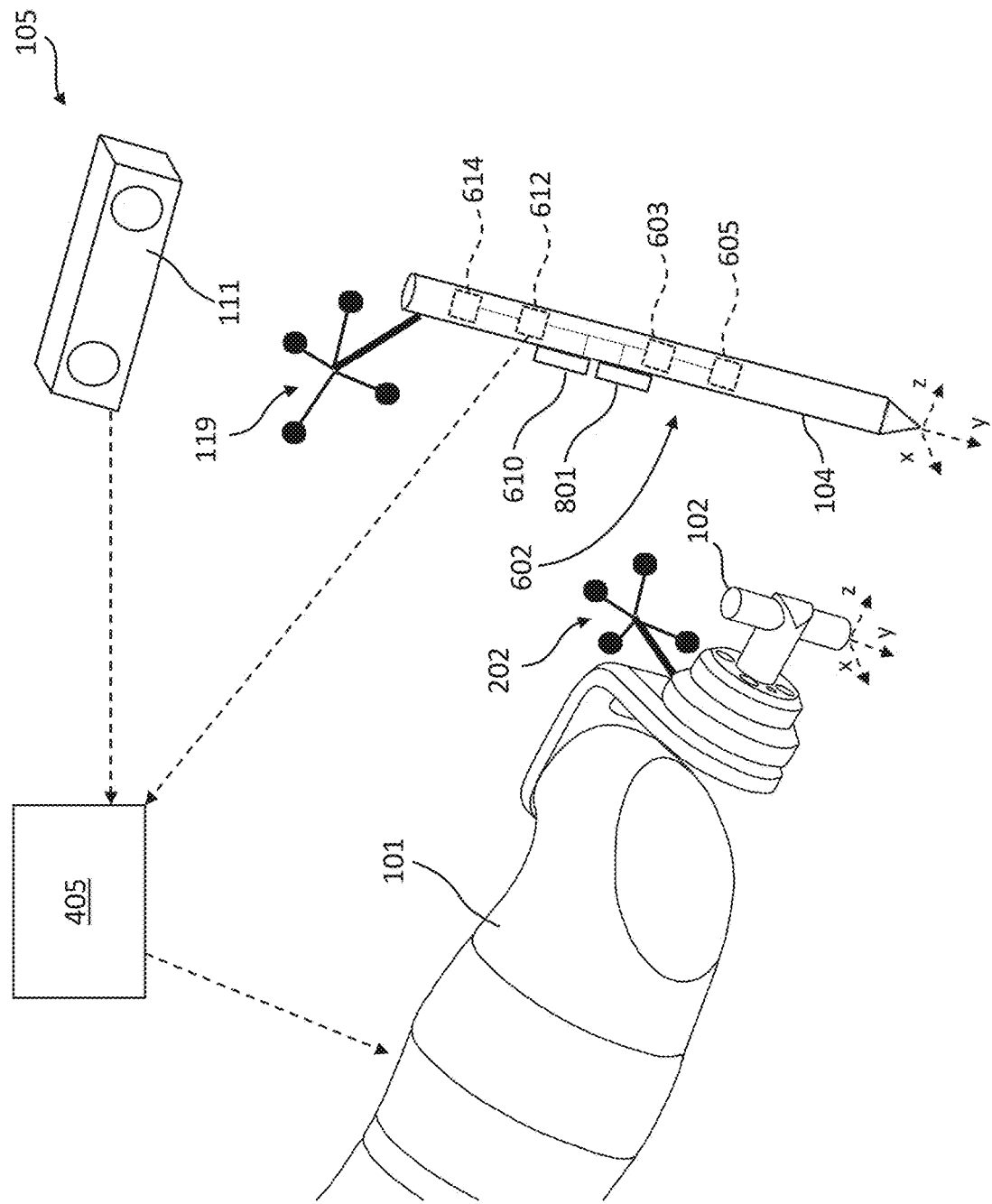
FIG. 8 illustrates a handheld device having a plurality of user input components on the handheld device.

FIG. 8 illustrates an embodiment of a handheld device 104 for controlling the movement of a robotic arm 101 in a "follow" mode as described above. The handheld device 104 in this embodiment includes a plurality of user input components (i.e., buttons 610 and 801). The plurality of user input components 610, 801 may be used to control and modify the motion scaling between movements of the handheld device 104 and the corresponding movements of the robotic arm 101. For example, while a first button 610 is pressed by the user, the robotic control system 405 may apply a first motion scaling factor for movement of the robotic arm 101 (e.g., to provide gross movements of the arm) and when a second button 801 is pressed by the user, the robotic control system 405 may apply a second motion scaling factor for movement of the robotic arm 101 (e.g., to provide fine movements of the arm). The plurality of user input components 610, 801 may be coupled to circuitry 612 configured to detect an input event (i.e., button push) at each user input component 610, 801 and to transmit signals to the robotic control system 405. In some embodiments, the circuitry 612 may include wireless transceiver circuitry 614 configured to transmit the signals wirelessly. Alternately, the handheld device 104 may be coupled to the robotic control system 405 via a wired link.

Figure 9:
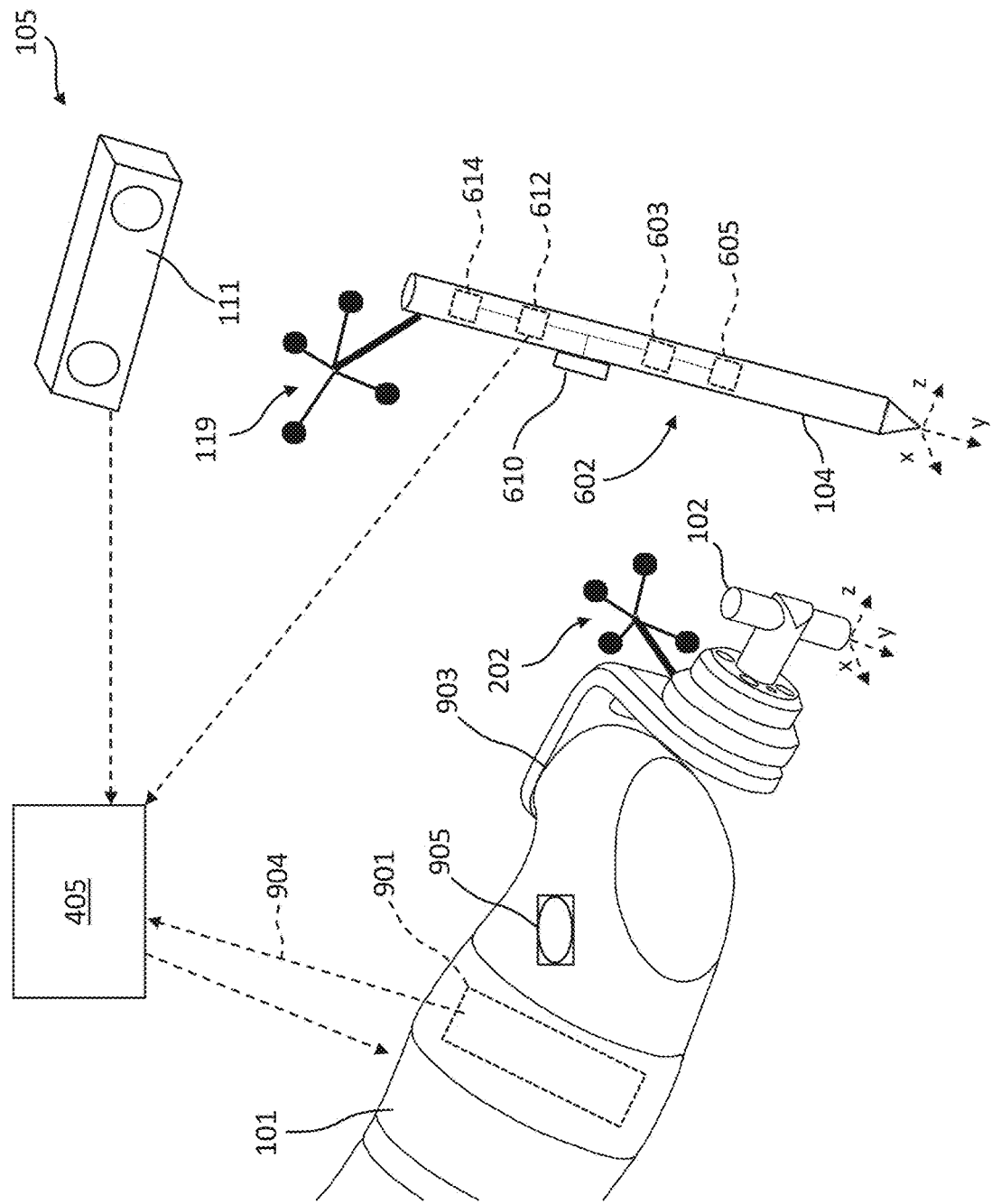
FIG. 9 illustrates a surgical robotic system that includes a robotic arm having a force sensor for detecting a force or torque applied to the robotic arm and a handheld device having a marker device that enables the handheld device to be tracked by a motion tracking system.

FIG. 9 illustrates a further embodiment of a surgical robotic system 900 that includes a robotic arm 101 having a force sensor 901 for detecting a force applied to the robotic arm 101 and a handheld device 104 having a marker device 119 that enables the handheld device 104 to be tracked using a motion tracking system 105, as described above. The force sensor 901 may be a multi-axis (e.g., six degree of freedom) force and torque sensor that is configured to measure the forces and torques applied to the robotic arm 101. The forces and torques measured by the force sensor 901 may be provided to a robotic control system 405, as described above. In embodiments, the system may operate in a "handguiding" mode in which the robotic control system 405 may control the movement of the robotic arm 101 in response to the threes and/or torques measured by the force sensor 901. This may enable the user to manually adjust the configuration of the robotic arm, including the position and/or orientation of the end effector 102.

In the embodiment of FIG. 9, a multi-axis force/torque sensor 901 (e.g., transducer) may be mounted within the robotic arm 101. In this embodiment, the force/torque sensor 901 is mounted behind the distal-most joint 903 of the robotic arm 101, although it will be understood that the sensor 901 rimy be located in another suitable location, such as between the distal-most joint 903 of the robotic arm 101 and the end effector 102. The sensor 901 may be configured to output an electronic signal in response to a force received at the sensor 901 (e.g., via a user grasping and applying a force to the distal end of the robotic arm 101). The output signal from the sensor 901 may represent the magnitude of the applied force along the x-, y- and z-axes as well as the associated torques about these axes. The output signal from the sensor 901 may be provided to the robotic control system via a communication path 904, which may be a wire/cable link extending along the length of the robotic arm 101 or a wireless link. The robotic control system 405 may plan a movement of the robotic arm 101 based on the signal received from the sensor 901. For example, in response to a measured force and/or torque signal, the robotic control system 405 may plan and execute a corresponding motion of the robotic arm 101 to cause the end effector 102 to move in the direction of the applied force/torque. This process may occur repeatedly so that the user may manually move the end effector 102 to desired positions and orientations. In some embodiments, the robotic control system 405 may be configured to Move the arm in "handguiding" mode only when the applied force/torque measured at the sensor 901 exceeds a pre-determined threshold value. In addition, the robotic control system 901 may also be configured to compensate for forces due to gravity on the robotic arm 101. The robotic control system 405 may also apply a collision model to prevent the robotic arm 101 from colliding with the patient or other objects when being moved in handguiding mode.

The system shown in FIG. 9 may also operate in a "follow" mode in which the robotic control system 405 may control the movement of the robotic arm 101 in response to the tracked movements of the handheld device 104, as is described above. In embodiments, the robotic control system 405 may alternate between operation in "handguiding" mode and "follow" mode based on an input event from the user (e.g., a voice command, a touch event on a display screen, a button push, a mouse/keyboard click, depression of a foot pedal, etc.). In some embodiments, while the system is operating in "follow" mode as described above, the robotic control system 405 may automatically exit "follow" mode and enter "handguiding" mode in response to a triggering event, such as the force sensor 901 measuring a force or torque on the robotic arm 101 above a pre-determined threshold. Alternately, while operating in "handguiding" mode, the robotic control system 405 may automatically exit "handguiding" mode and enter "follow" mode in response to a triggering event, such as the user bringing a specialized handheld device 104 used for moving the robotic arm 101 in "follow" mode within the range (e.g., field-of-view) of the motion tracking system 105. Operation in either or both of "handguiding" mode and "follow" mode may require continuous activation by the user, such as holding down a button or footpedal.

In various embodiments, the "handguiding" mode may be used for gross movements of the robotic arm 101, and the "follow" mode may be used to make precise adjustments to the position and/or orientation of the end effector 102. In both the handguiding mode and the follow mode, the robotic arm 101 may be forward driven by the robotic control system 405 without requiring any backdriving of the joints.

In certain embodiments, the handheld device 104 may be removably mounted (i.e., docked) to the robotic arm 101, such as within a docking station 905 located on the robotic arm 101. The robotic control system 405 may be configured to determine whether or not the handheld device 104 is mounted within the docking station 905 on the robotic arm 101. The robotic control system 405 may operate the robotic arm 101 in handguiding mode while the handheld device 104 is mounted within the docking station 905. When the handheld device 104 is removed from the docking station 905, the robotic control system 405 may exit handguiding mode and operate the arm in follow mode until the user replaces the handheld device 104 within the clocking station 905.

In further embodiments, a force/torque sensor 901 as described above tray be operatively coupled to a handheld device 104 when the handheld device 104 is docked in a docking station 905 on the robotic arm 101. The force/torque sensor 901 may be configured to measure forces and/or torques applied by the user to the handheld device 104 docked within the docking station 905, and the robotic control system 405 may move the arm in response to these measured forces and/or torques. When the handheld device 104 is docked in the docking station 905, it may be used to control the motions of robotic arm in the manner of a joystick or a three-dimensional mouse. When the handheld device 104 is removed from the docking station 905, it may be used to control the robotic arm in "follow" mode as described above.

Figure 10A:
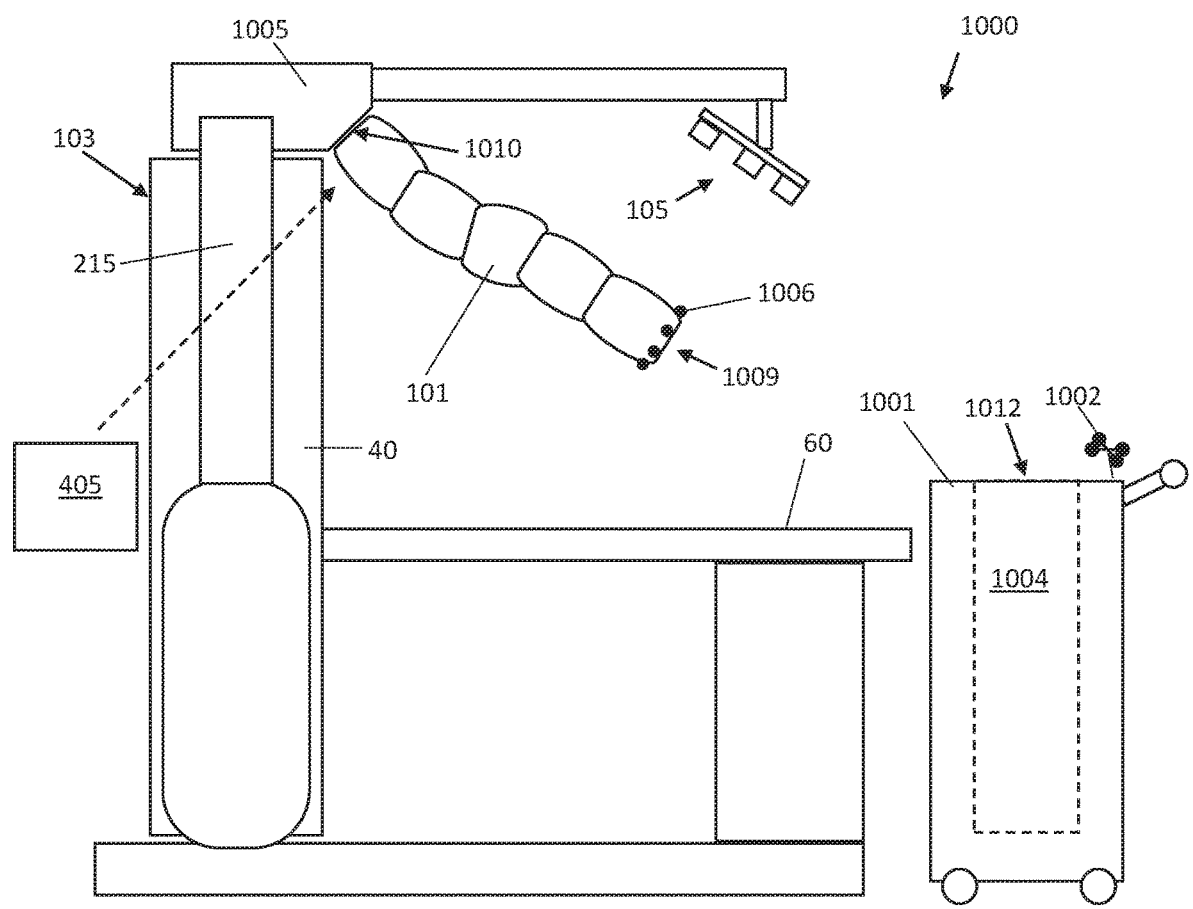
FIGS. 10A-10E illustrate a surgical robotic system that includes a robotic arm and a cart having a marker device that enables the cart to be tracked by a motion tracking system, where the robotic arm may be controlled to move to a transfer position based on the tracked location of the cart.

FIGS. 10A-10E illustrate a further embodiment of a surgical robotic system 1000 that includes a robotic arm 101 and a cart 1001 for storing and transporting the robotic arm 101 when not in use. As shown in FIG. 10A, the robotic arm 101 may be mounted in a suitable location to enable the robotic arm 101 to move throughout the surgical field to assist in the performance of a surgical procedure. In this embodiment, the robotic arm 101 is mounted to an imaging device 103. In particular, the base of the robotic arm 101 is attached to a mounting surface 1010 that is supported by a support element 215 (a curved rail) that extends over the top surface of imaging device 103. The mounting surface 1010 may be a surface of a movable carriage 1011 that be movable along the length of the support element 215. Alternately, the robotic arm 101 may be directly attached to the imaging device 103, such as to the gantry 40 or patient support 60, or to another structure in the operating room, such as the wall, ceiling or floor. The robotic arm 101 may be attached to a mounting surface 1010 using bolts or similar mechanical fasteners that may enable the robotic arm 101 to be removed when not in use. The robotic arm 101 may be removed from the mounting surface 1010 and stored on or within a cart 1001 when it is not in use. The cart 1001 may be a mobile cart to facilitate transport of the robotic arm 101. The cart 1001 for the robotic arm 101 may be a cart 120 as described above with reference to FIG. 1 that may also include, for example, a monitor display, user input(s)/control(s) and system electrical components (e.g., a computer). Alternately, the cart 1001 for storage/transport of the robotic arm 101 may be separate from a cart 120 as described with reference to FIG. 1.

In some cases, it may be difficult and time-consuming to safely transfer the robotic arm 101 between the mounting surface 1010 to which the robotic arm 101 is attached during use and a cart 1001 used for storage and transport of the robotic arm 101. In the embodiment of FIGS. 10A-10E, the cart 1001 includes a marker device 1002 that enables the cart 1001 to be tracked by a motion tracking system 105, as described above. The robotic control system 405 may be configured to control the robotic arm 101 to cause the robotic arm 101 to move to a transfer position based on the tracked position of the cart 1001. The transfer position of the robotic arm 101 may be a position that facilitates the transfer of the robotic arm 101 from the mounting surface 1010 to the cart 1001.

In FIG. 10A, the robotic arm 101 is shown attached to the mounting surface 1010 above the gantry 40 of the imaging system 103 and the cart 1001 is located a distance away from the imaging system 103, outside of the range (field-of-view) of the motion tracking system 105. The motion tracking system 105 may track the robotic arm 101 in three-dimensional space via a plurality of markers 1006 located on the robotic arm 101. A robotic control system 405 may control the robotic arm 101 to move the arm to a desired pose within the three-dimensional space.

Figure 10B:
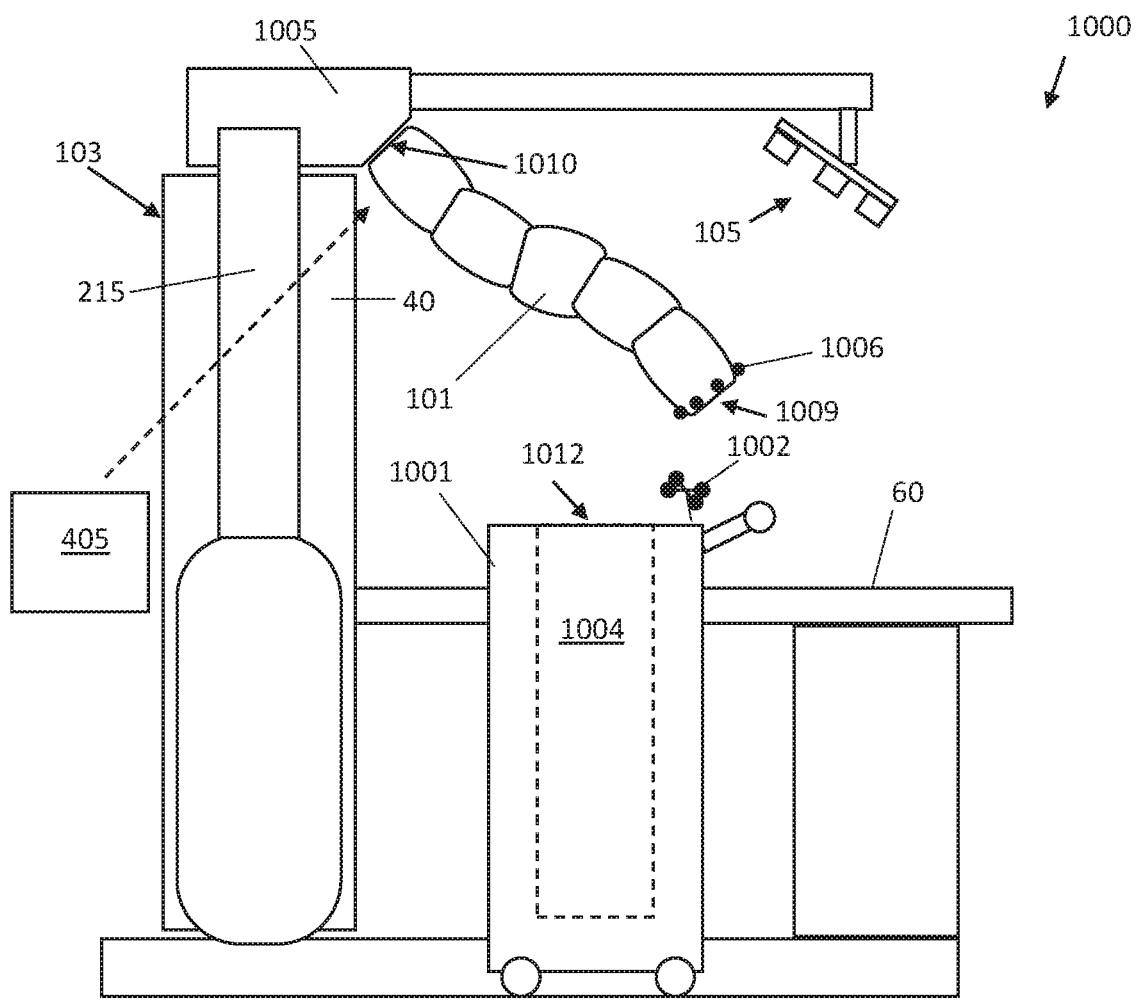

In FIG. 10B, the cart 1001 is moved adjacent to the imaging system 103 such that the marker device 1002 is within the range (field-of-view) of the motion tracking system 105. The motion tracking system 105 may track the location of the cart 1001 in the same coordinate system as the robotic arm 101. The cart 1001 may be pre-calibrated so that the spatial relationship between the marker device 1002 and a target location. 1012 on or adjacent to the cart 1001 is known within the common coordinate system. The target location 1012 may be a location to which the robotic arm 101 may be moved to in order to facilitate transfer of the robotic arm 101 to the cart 1001. In the embodiment of FIG. 10B, the target location 1012 is an entrance to a housing 1004 in the cart 1001 that is configured to receive and house the robotic arm 101. In other embodiments, the target location 1012 may be associated with a cradle or other mechanism for securely holding the robotic arm 101 for storage and/or transport.

Figure 10C:
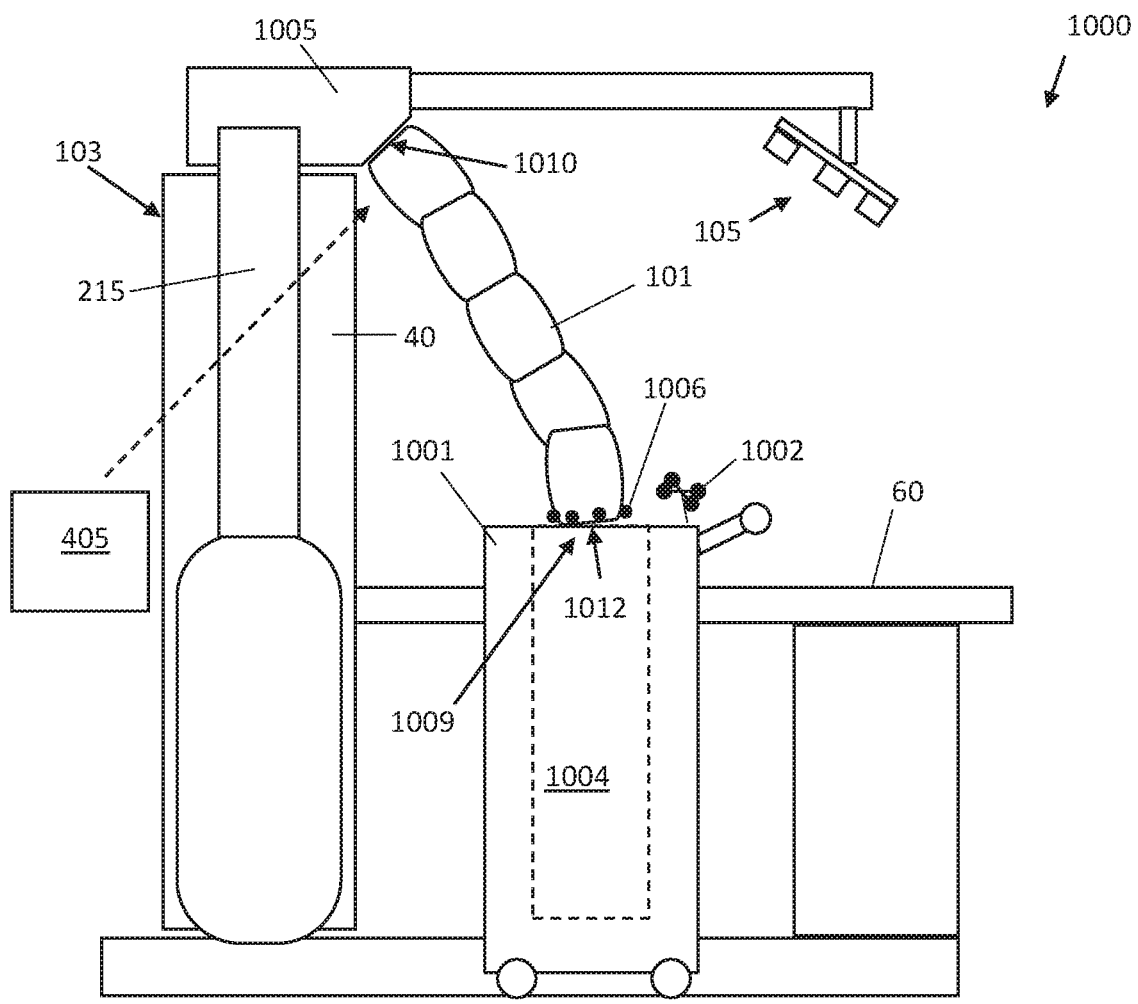
Figure 10D:
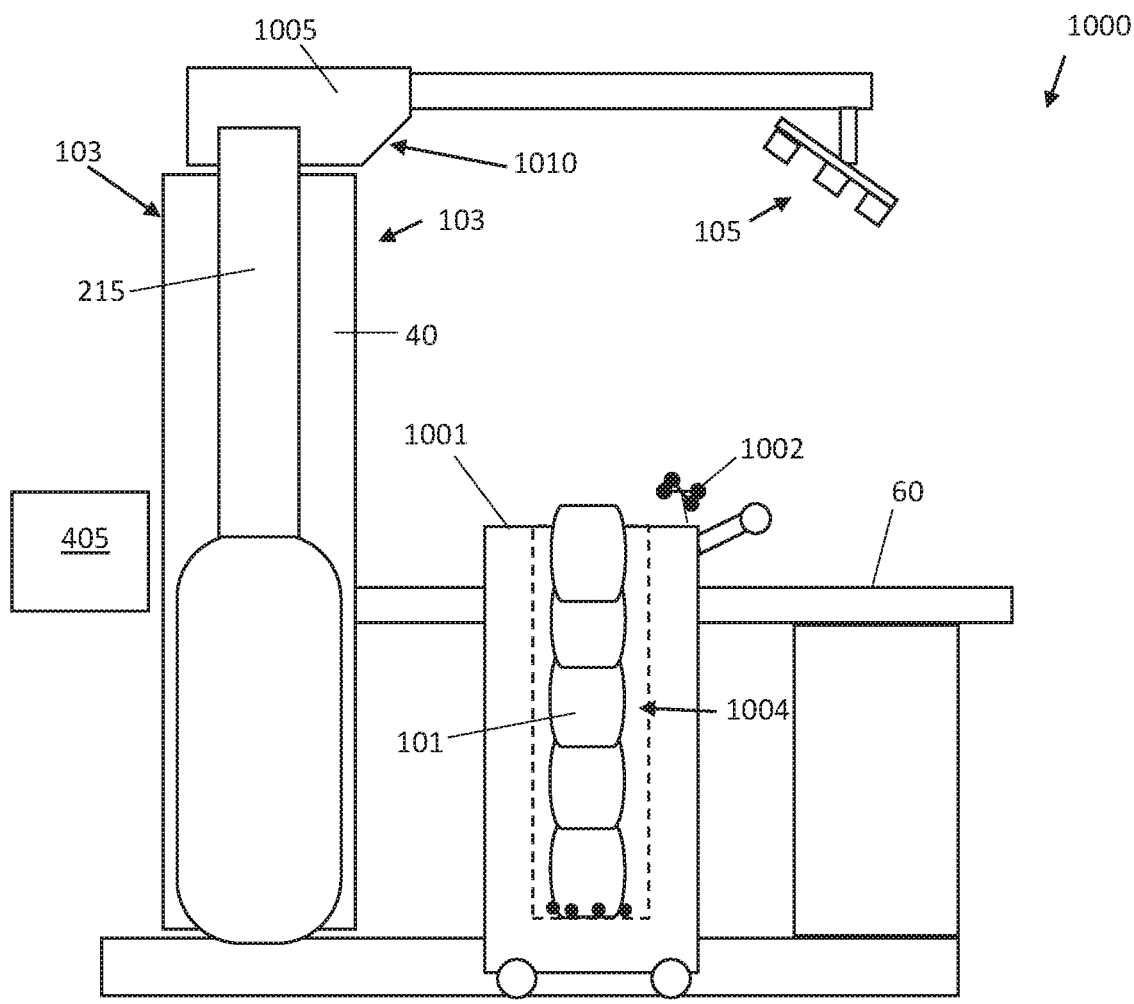

In embodiments, as the cart approaches the robotic arm 101, the motion tracking system 105 may track the position of the cart 1001 and may optionally provide user feedback (e.g., an audio alert, a visual indicator on the robotic arm 101 and/or a display screen) when the target location 1012 is at a location that is suitable for transferring the robotic arm 101 to the cart 1001. To transfer the robotic arm 101 to the cart 1001, the robotic control system 405 may control the robotic arm 101 to move the distal end 1009 of the arm 101 to the target location 1012, as shown in FIG. 10C. This may occur in response to a user input event. The user may then disconnect the robotic arm 101 from the mounting surface 1010 and the arm 101 may be lowered into the housing 1004 as shown in FIG. 10D.

Figure 10E:
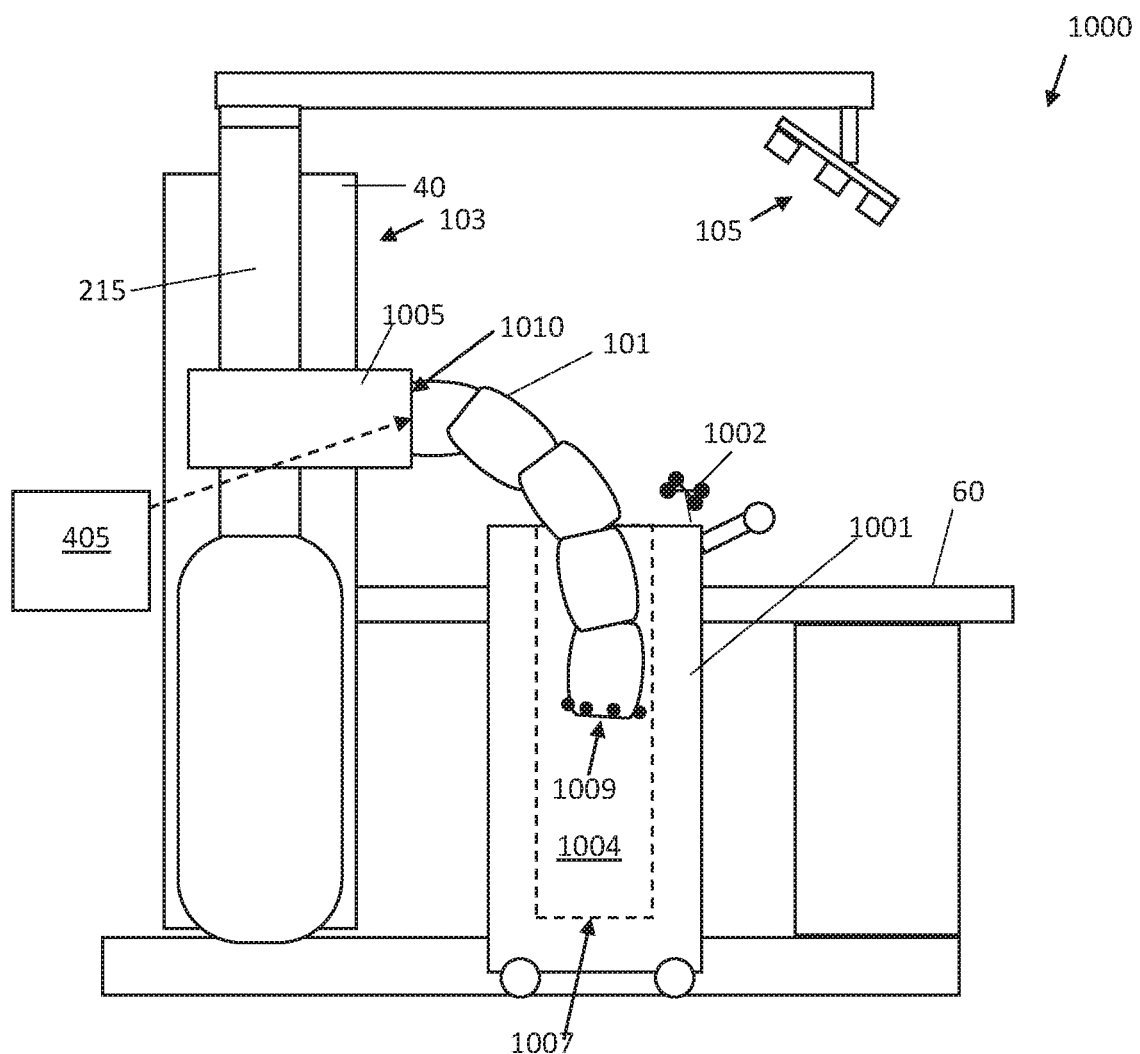

Alternately, the robotic control system 405 may control the robotic arm 101 to move the arm 101 partially or completely into a holding mechanism on or within the cart 1001. This is illustrated in FIG. 10E, which shows the robotic arm 101 moved partially into the housing 1004 of the cart 1001. In this embodiment, the carriage 1005 to which the robotic arm 101 is attached is lowered on the support element 215 (i.e., curved rail) to a position on a side of gantry 40. From this position, the robotic arm 101 may reach at least partially inside the housing 1004 of the cart. This process may be fully automated, such that the carriage 1005 is motorized and configured move to a pre-set loading/unloading position on the support element 215. A quick-connect/disconnect mechanism may be used for mechanically and electrically coupling and decoupling the robotic arm 101 from the mounting surface 1010 on the carriage 1005.

The cart 1001 may optionally include a mechanism (e.g., a platform 1007 that raises and lowers within the housing 1004) that is configured to at least partially lift the robotic arm 101 from the housing 1004 to enable the robotic arm 101 to more easily dock to the carriage 1005. Once the robotic arm 101 is mechanically and electrically connected to the mounting surface 1010 on the carriage 1005, the robotic control system 405 may control the robotic arm 101 to cause the entire arm 101 to move out of the housing 1004 in the cart 1001. The carriage 1005 may optionally move on the support element 215 to position the robotic arm 101 in a suitable location for performing robotically-assisted image-guided surgery.

Figure 11:
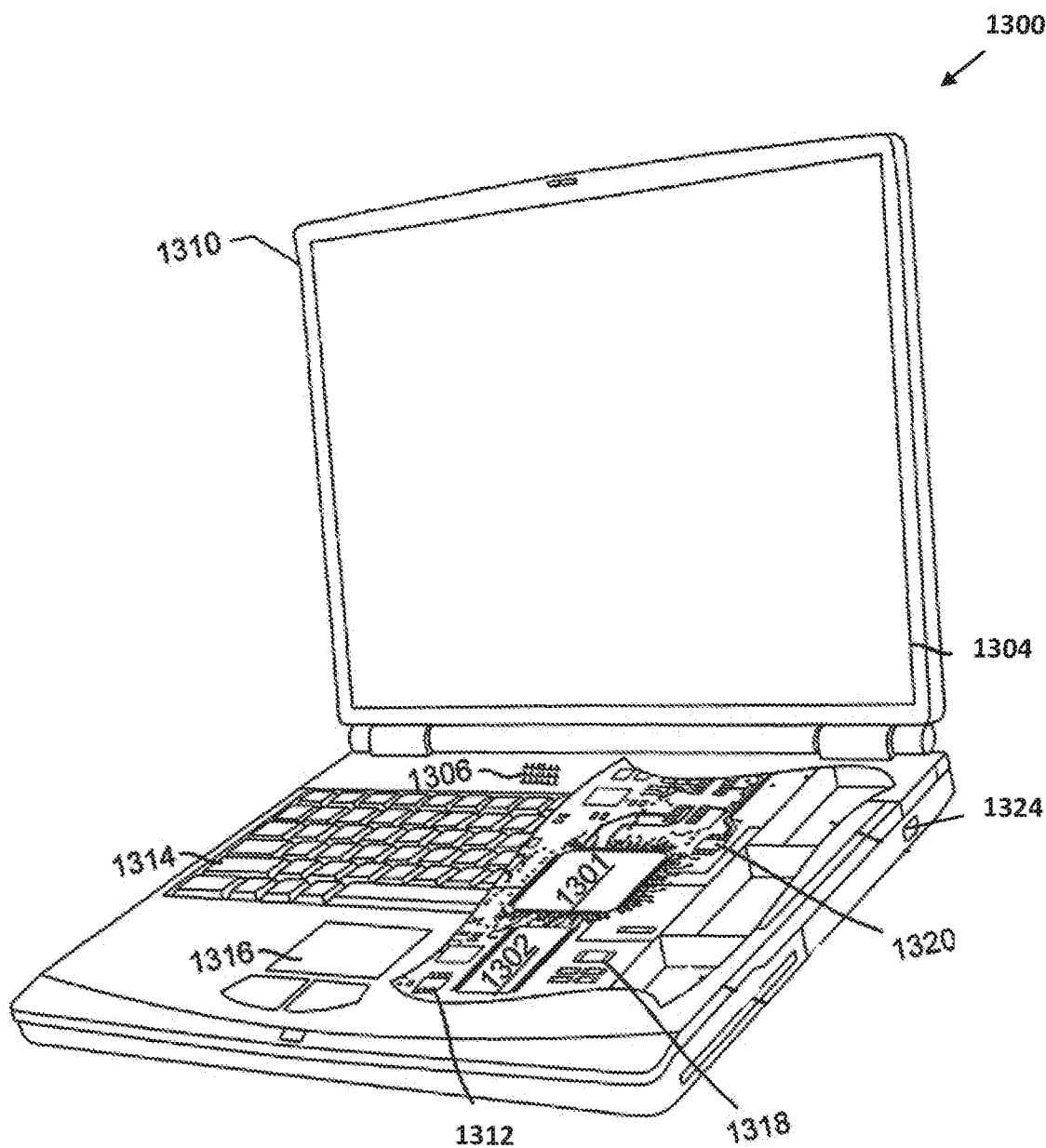
FIG. 11 schematically illustrates a computing device which nay be used for performing various embodiments.

FIG. 11 is a system block diagram of a computing device 1300 useful for performing and implementing the various embodiments described above. The computing device 1300 may perform the functions of an image guided surgery system 400 and/or a robotic control system 405, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a non-volatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM. CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for transferring a robotic arm from a mounting surface to which the robotic arm is attached during use to a mobile cart for storage and/or transport of the robotic arm, the method comprising:
   tracking the location of the mobile cart relative to the robotic arm using a motion tracking system comprising an optical sensor device;
   determining the arrangement of a joint disposed between linkages of the robotic arm based on signals from an encoder associated with the joint; and
   controlling the robotic arm to move at least one linkage of the robotic arm to place the robotic arm into a pose that facilitates transferring the robotic arm from the mounting surface to the mobile cart based on the tracked location of the mobile cart determined with the optical sensor device.

2. The method of claim 1, wherein the mobile cart comprises a marker device that enables the mobile cart to be tracked in three-dimensional space by the optical sensor device.

3. The method of claim 1, wherein controlling the robotic arm includes controlling the robotic arm to move at least one linkage of the robotic arm to arrange a distal end of the robotic arm at a target location based on the tracked location of the mobile cart.

4. The method of claim 3, wherein the target location is aligned with an entrance to a housing in the mobile cart configured to receive the robotic arm within the housing.

5. The method of claim 4, wherein the mobile cart includes a platform disposed within the housing; and
   wherein the method further comprises supporting the robotic arm on the platform within the housing.

6. The method of claim 5, further comprising raising the platform within the housing to at least partially lift the robotic arm from the housing.

7. The method of claim 3, further comprising providing user feedback with an indicator when the target location is at a location for transferring the robotic arm to the mobile cart.

8. The method of claim 3, wherein controlling the robotic arm to move the distal end of the robotic arm to the target location occurs in response to a user input event occurring based on user engagement with a user input device.

9. The method of claim 1, wherein the mounting surface is located on a carriage that is moveable along a support element of an imaging device; and
   wherein the method further comprises moving the carriage and the robotic arm together along the support element of the imaging device to a pre-determined loading/unloading position.

10. The method of claim 1, wherein the robotic arm comprises a marker device that enables the robotic arm to be tracked in three-dimensional space by the optical sensor device.

11. A system for robot-assisted surgery, comprising:
    a robotic arm including a joint arranged between linkages, and an encoder associated with the joint;
    a mounting surface to which the robotic arm is attached during use;
    a mobile cart arranged to receive the robotic arm for storage and/or transport;
    a motion tracking system configured to track the location of the mobile cart relative to the robotic arm, the motion tracking system comprising an optical sensor device; and
    a controller coupled to the robotic arm and to the motion tracking system, the controller comprising a processor configured with processor-executable instructions to perform operations comprising:
      tracking the location of the mobile cart relative to the robotic arm using the motion tracking system;
      determining the arrangement of the joint of the robotic arm based on signals from the encoder; and
      controlling the robotic arm to move at least one linkage of the robotic arm to place the robotic arm into a pose that facilitates transferring the robotic arm from the mounting surface to the mobile cart based on the tracked location of the mobile cart determined with the optical sensor device.

12. The system of claim 11, wherein the mobile cart comprises a marker device that enables the mobile cart to be tracked in three-dimensional space by the optical sensor device.

13. The system of claim 11, wherein the controller is further configured to control the robotic arm to move at least one linkage of the robotic arm to arrange a distal end of the robotic arm at a target location based on the tracked location of the mobile cart.

14. The system of claim 13, further comprising an indicator coupled to the controller; and
    wherein the controller is further configured to activate the indicator to provide user feedback when the target location is at a location for transferring the robotic arm to the mobile cart.

15. The system of claim 14, wherein the indicator is configured to provide user feedback as an audio and/or visual alert.

16. The system of claim 13, further comprising a user input device coupled to the controller; and
    wherein the controller is further configured to move the distal end of the robotic arm to the target location in response to a user input event occurring based on user engagement with the user input device.

17. The system of claim 13, wherein the mobile cart includes a housing configured to receive the robotic arm within the housing for storage and/or transport; and
    wherein the target location is aligned with an entrance to the housing in the mobile cart.

18. The system of claim 17, wherein the mobile cart further includes a platform disposed within the housing for supporting the robotic arm.

19. The system of claim 18, wherein the platform is movable within the housing to at least partially lift the robotic arm from the housing when the platform is raised.

20. The system of claim 11, further comprising an imaging device configured to obtain diagnostic images of a patient, the imaging device including a base, an O-shaped gantry movably coupled to the base, and a support element extending over an outer surface of the O-shaped gantry; and
    wherein the mounting surface is located on a carriage that is movable along the support element of the imaging device, with the carriage and the robotic arm being movable together along the support element to a predetermined loading/unloading position.

* * * * *